(12) United States Patent
Peterson et al.

(10) Patent No.: US 11,396,516 B2
(45) Date of Patent: Jul. 26, 2022

(54) TRICYCLIC COMPOUNDS AS CYP1 INHIBITORS

(71) Applicant: The General Hospital Corporation, Boston, MA (US)

(72) Inventors: Randall T. Peterson, Salt Lake City, UT (US); Aarti Asnani, Arlington, MA (US); Yan Liu, Boston, MA (US); Baohui Zheng, Boston, MA (US); You Wang, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 141 days.

(21) Appl. No.: 16/622,588

(22) PCT Filed: Jun. 15, 2018

(86) PCT No.: PCT/US2018/037770
§ 371 (c)(1),
(2) Date: Dec. 13, 2019

(87) PCT Pub. No.: WO2018/232251
PCT Pub. Date: Dec. 20, 2018

(65) Prior Publication Data
US 2021/0163495 A1    Jun. 3, 2021

Related U.S. Application Data

(60) Provisional application No. 62/521,114, filed on Jun. 16, 2017.

(51) Int. Cl.
| | | |
|---|---|---|
| C07D 493/04 | (2006.01) | |
| A61P 35/04 | (2006.01) | |
| A61K 31/704 | (2006.01) | |
| A61K 45/06 | (2006.01) | |

(52) U.S. Cl.
CPC .......... *C07D 493/04* (2013.01); *A61K 31/704* (2013.01); *A61K 45/06* (2013.01); *A61P 35/04* (2018.01)

(58) Field of Classification Search
CPC ...... A61K 31/704; A61K 35/04; A61K 45/06; C07D 493/04
See application file for complete search history.

(56) References Cited

U.S. PATENT DOCUMENTS

| | | |
|---|---|---|
| 5,304,121 A | 4/1994 | Sahatjian |
| 5,886,026 A | 3/1999 | Hunter et al. |
| 6,099,562 A | 8/2000 | Ding |
| 6,803,031 B2 | 10/2004 | Rabinowitz |
| 9,119,858 B2 | 9/2015 | Yan et al. |
| 9,650,678 B2 | 5/2017 | Bhatia |
| 2013/0242924 A1 | 9/2013 | Kim et al. |
| 2013/0252924 A1 | 9/2013 | Penninger et al. |
| 2015/0150843 A1 | 6/2015 | Peterson et al. |

FOREIGN PATENT DOCUMENTS

WO    WO 2014/194285    12/2014

OTHER PUBLICATIONS

Liu et al., "Visnagin protects against doxorubicin-induced cardiomyopathy through modulation of mitochondrial malate dehydrogenase", Science Translational Medicine, vol. 6, No. 266, pp. 1-3 (2014).*
Asselin et al., "Cardioprotection and Safety of Dexrazoxane in Patients Treated for Newly Diagnosed T-Cell Acute Lymphoblastic Leukemia or Advanced-Stage Lymphoblastic Non-Hodgkin Lymphoma: A Report of the Children's Oncology Group Randomized Trial Pediatric Oncology Group 9404," Journal of Clinical Oncology: Official Journal of the American Society of Clinical Oncology, Mar. 2016, 34(8):854-862.
Bruno et al., "Targeting cytochrome P450 enzymes: a new approach in anti-cancer drug development," Bioorganic & Medicinal Chemistiy, Aug. 2007, 15(15):5047-5060.
Cardinale et al., Early detection of anthracycline cardiotoxicity and improvement with heart failure therapy. Circulation, Jun. 2015, 131(22):1981-1988.
César et al., "Minor Furanocoumarins and Coumarins in Grapefruit Peel Oil as Inhibitors of Human Cytochrome P450 3A4," J. Nat. Prod., Aug. 2009, 72:1702-1704.
Chen et al., "Imaging of apoptosis in the heart with nanoparticle technology," Wiley Interdisciplinary Reviews Nanomedicine and Nanobiotechnology, Jan. 2011, 3(1):86-99.
Claycomb et al., "HL-1 cells: a cardiac muscle cell line that contracts and retains phenotypic characteristics of the adult cardiomyocyte," Proceedings of the National Academy of Sciences of the United States of America, Mar. 1998, 95(6):2979-2984.
Dabir et al., "Aryl hydrocarbon receptor is activated by glucose and regulates the thrombospondin-1 gene promoter in endothelial cells," Circulation Research, Jun. 2008, 102(12): 1558-1565.
Divanovic et al., "Contributions of the three CYP1 monooxygenases to pro-inflammatory and inflammation-resolution lipid mediator pathways," Journal of Immunology, Sep. 2013, 191(6):3347-3357.
Ghosh & Brindisi., "Organic carbamates in drug design and medicinal chemistry," Journal of Medicinal Chemistiy, Jan, 2015, 58(7):2895-2940.
Goldstone et al., "Identification and developmental expression of the full complement of Cytochrome P450 genes in Zebrafish," BMC Genomics, Dec. 2010, 11(1):643.
Goodale et al., "Ligand-Specific Transcriptional Mechanisms Underlie Aryl Hydrocarbon Receptor-Mediated Developmental Toxicity of Oxygenated PAHs," Toxicological Sciences, 147(2):397-411.
Hasinoff & Herman., "Dexrazoxane: how it works in cardiac and tumor cells. Is it a prodrug or is it a drug?" Cardiovasc. Toxicol., Jun. 2007, 7(2): 140-144.
Ichikawa et al., "Cardiotoxicity of doxorubicin is mediated through mitochondrial iron accumulation," The Journal of Clinical Investigation, Feb. 2014, 124(2):617-630.

(Continued)

*Primary Examiner* — Kevin E Weddington
(74) *Attorney, Agent, or Firm* — Fish & Richardson P.C.

(57) ABSTRACT

The present application provides tricyclic compounds useful, e.g., in treating or preventing cardiotoxicity and cardiomyopathy in patients undergoing cardiotoxic chemotherapy. Methods of making and using the tricyclic compounds to treat cancer are also described.

8 Claims, 16 Drawing Sheets

(56) References Cited

OTHER PUBLICATIONS

Illum, "Is nose-to-brain transport of drugs in man a reality?" J. Pharm. Pharmacol, Jan. 2004, 56:3-17.
Illum, "Transport of drugs from the nasal cavity to the central nervous system," Eur. J. Pharm. Sci. Jul. 2000, 11(1):1-18.
Imondi et al., "Dose-response relationship of dexrazoxane for prevention of doxorubicin-induced cardiotoxicity in mice, rats, and dogs," Cancer Research, Sep. 1996, 56(18):4200-4204.
Imondi, "Preclinical models of cardiac protection and testing for effects of dexrazoxane on doxorubicin antitumor effects," Seminars in Oncology, Aug. 1998, 25(4):22-30.
Jenkins et al., "Eicosanoid signaling pathways in the heart," Cardiovascular Research, Dec. 2008, 82(2):240-249.
Jönsson et al., "Basal and 3,3',4,4',5-pentachlorobiphenyl-induced expression of cytochrome P450 1A, 1B and 1C genes in zebrafish," Toxicology and Applied Pharmacology, May 2007, 221(1):29-41.
Liehr and Ricci, "4-Hydroxylation of estrogens as marker of human mammary tumors," Proceedings of the National Academy of Sciences of the United States of America, Apr. 1996, 93(8):3294-3296.
Liu et al., "Cytochrome P450 family 1 inhibitors and structure-activity relationships," Molecules, Dec. 2013, 18(12): 14470-14495.
Liu et al., "Visnagin protects against doxorubicin-induced cardiomyopathy through modulation of mitochondrial malate dehydrogenase," Science Translational Medicine, Dec. 2014, 6(266):266ra170-266ra170, 13 pages.
Lyn et al., "Topoisomerase IIβ-mediated DNA double-strand breaks: implications in doxorubicin cardiotoxicity and prevention by dexrazoxane," Cancer Research, Sep. 2007, 67(18):8839-8846.
Maayah et al., "CYP1B1 inhibition attenuates doxorubicin-induced cardiotoxicity through a mid-chain HETEs-dependent mechanism," Pharmacological Research, Mar. 2016, 105:28-43.
Mitani et al., "Doxorubicin cardiotoxicity: prevention of congestive heart failure with serial cardiac function monitoring with equilibrium radionuclide angiocardiography in the current era," Journal of Nuclear Cardiology, Mar. 2003, 10(2): 132-139.
Moieni-Arya et al., "Effect of Osthole and oxypeucedanin on doxorubicin—induced apoptosis in PC12 cells," Research in Pharmaceutical Sciences, Sep. 2012, 7(5):1018.
Murray et al., "Tumor-specific expression of cytochrome P450 CYP1B1," Cancer Research, Jul. 1997, 57(14):3026-3031.

PCT International Preliminary Report on Patentability in International Appln. No. PCT/US2018/037770, dated Dec. 17, 2019, 9 pages.
PCT International Search Report and Written Opinion in International Appln. No. PCT/US2018/037770, dated Oct. 4, 2018, 12 pages.
Phuwapraisirisan et al., "A Novel Furanocoumarin from Feroniella lucida Exerts Protective Effect against Lipid Peroxidation," Phytother. Res., May 2006, 20:708-710.
Seif et al., "Dexrazoxane exposure and risk of secondary acute myeloid leukemia in pediatric oncology patients," Pediatric Blood & Cancer, Apr. 2015, 62(4):704-709.
Shimada & Fujii-Kuriyama, "Metabolic activation of polycyclic aromatic hydrocarbons to carcinogens by cytochromes P450 1A1 and 1B1," Cancer Science, Jan. 2004, 95(1):1-6.
Suliman et al., "The CO/HO system reverses inhibition of mitochondrial biogenesis and prevents murine doxorubicin cardiomyopathy," The Journal of Clinical Investigation, Dec. 2007, 117(12):3730-3741.
Swain et al., "Cardioprotection with dexrazoxane for doxorubicin-containing therapy in advanced breast cancer," Journal of Clinical Oncology, Apr. 1997, 15(4):1318-1332.
Tebbi et al., "Dexrazoxane-associated risk for acute myeloid leukemia/myelodysplastic syndrome and other secondary malignancies in pediatric Hodgkin's disease," Journal of Clinical Oncology, Feb. 2007, 25(5):493-500.
Van Tiem and Di Giulio, "AHR2 knockdown prevents PAH-mediated cardiac toxicity and XRE-and ARE-associated gene induction in zebrafish (Danio rerio)," Toxicology and Applied Pharmacology, 254(3):280-287.
Volkova et al., "Activation of the aryl hydrocarbon receptor by doxorubicin mediates cytoprotective effects in the heart," Cardiovascular Research, Jan. 2011, 90(2):305-314.
Wallace, "Doxorubicin-induced cardiac mitochondrionopathy," Pharmacology & Toxicology, Sep. 2003, 93(3):105-115.
Zhang et al., "Identification of the molecular basis of doxorubicin-induced cardiotoxicity," Nature Medicine, Nov. 2012, 18(11):1639-1642.
Zhou et al., "Cumulative and irreversible cardiac mitochondrial dysfunction induced by doxorubicin," Cancer Research, Jan. 2001, 61(2):771-777.
EP Extended European Search Report in European Appln. No. 18818129.1, dated Mar. 4, 2021, 7 pages.

* cited by examiner

TRICYCLIC COMPOUNDS AS CYP1 INHIBITORS

CLAIM OF PRIORITY

This application is a § 371 National Stage Application of PCT/US2018/037770, filed Jun. 15, 2018, which claims the benefit of U.S. Provisional Application Ser. No. 62/521,114, filed on Jun. 16, 2017. The entire contents of the foregoing application is incorporated herein by reference.

TECHNICAL FIELD

This invention relates to tricyclic compounds, and more particularly to furanochromone compounds that inhibit Cyp1 and/or induction of Cyp1.

BACKGROUND

Anthracyclines such as doxorubicin (DOX) are used to treat a number of common malignancies, including breast cancer, leukemia, lymphoma, and sarcoma. DOX exhibits potent tumoricidal activity but can also cause dose-dependent cardiotoxicity in up to 9% of patients, potentially resulting in congestive heart failure.

SUMMARY

In one general aspect, the present application provides a compound of Formula (I):

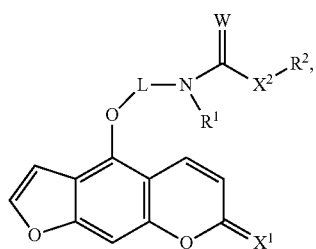

(I)

or a pharmaceutically acceptable salt thereof, wherein:

$X^1$ and $X^2$ are independently selected from O and S;

W is selected from O, S and $NR^1$;

L is selected from $C_{1-6}$ alkylene, $C_{2-6}$ alkenylene and $C_{2-6}$ alkynylene, each of which is optionally substituted with 1, 2, or 3 substituents independently selected from $R^a$;

$R^1$ is selected from H, $C_{1-3}$ alkyl, $C_{1-3}$ haloalkyl, $C_{2-4}$ alkenyl and $C_{2-4}$ alkynyl;

$R^2$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-14 membered heteroaryl, and 4-10 membered heterocycloalkyl, each of which is optionally substituted with 1, 2, or 3 substituents independently selected from $R^a$; and each $R^a$ is independently selected from OH, $NO_2$, CN, halo, $C_{1-3}$ alkoxy, $C_{1-3}$ haloalkoxy, $NH_2$, $C_{1-3}$ alkylamino and di($C_{1-3}$ alkyl)amino;

provided that the compound of Formula (I) is not a compound of formula:

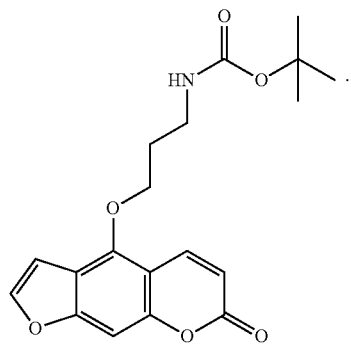 [SMILES: CC(C)(C)OC(=O)NCCCOc1c2ccoc2cc2oc(=O)ccc12]

In some embodiments, $X^1$ is O.

In some embodiments, $X^1$ is S.

In some embodiments, L is $C_{1-6}$ alkylene.

In some embodiments, the $C_{1-6}$ alkylene is linear.

In some embodiments, L is ethylene.

In some embodiments, $R^1$ is selected form H and $C_{1-3}$ alkyl.

In some embodiments, $R^1$ is H.

In some embodiments, W is selected from O and S.

In some embodiments, W is O.

In some embodiments, $X^2$ is O.

In some embodiments, $X^2$ is S.

In some embodiments, $R^2$ is selected from $C_{1-6}$ alkyl, $C_{1-6}$ haloalkyl, $C_{3-10}$ cycloalkyl and $C_{6-10}$ aryl, each of which is optionally substituted with 1, 2, or 3 substituents independently selected from $R^a$.

In some embodiments, $R^a$ is selected from OH, $NO_2$, CN, halo, $C_{1-3}$ alkoxy and $C_{1-3}$ haloalkoxy.

In some embodiments, $R^2$ is selected from $C_{1-6}$ alkyl and $C_{6-10}$ aryl.

In some embodiments, $R^2$ is selected from ethyl, tert-butyl, and phenyl.

In some embodiments:

$X^1$, $X^2$ and W are independently selected from O and S;

L is $C_{1-6}$ alkylene;

$R^1$ is selected form H and $C_{1-3}$ alkyl;

$R^2$ is selected from $C_{1-6}$ alkyl, $C_{1-6}$ haloalkyl, $C_{3-10}$ cycloalkyl and $C_{6-10}$ aryl, each of which is optionally substituted with 1, 2, or 3 substituents independently selected from $R^a$; and each $R^a$ is independently selected from OH, $NO_2$, CN, halo, $C_{1-3}$ alkoxy and $C_{1-3}$ haloalkoxy.

In some embodiments:

$X^1$ and $X^2$ are independently selected from O and S;

W is O;

L is selected form ethylene and propylene;

$R^1$ is H; and $R^2$ is selected from $C_{1-6}$ alkyl and $C_{6-10}$ aryl.

In some embodiments, the compound of Formula (I) is selected from:

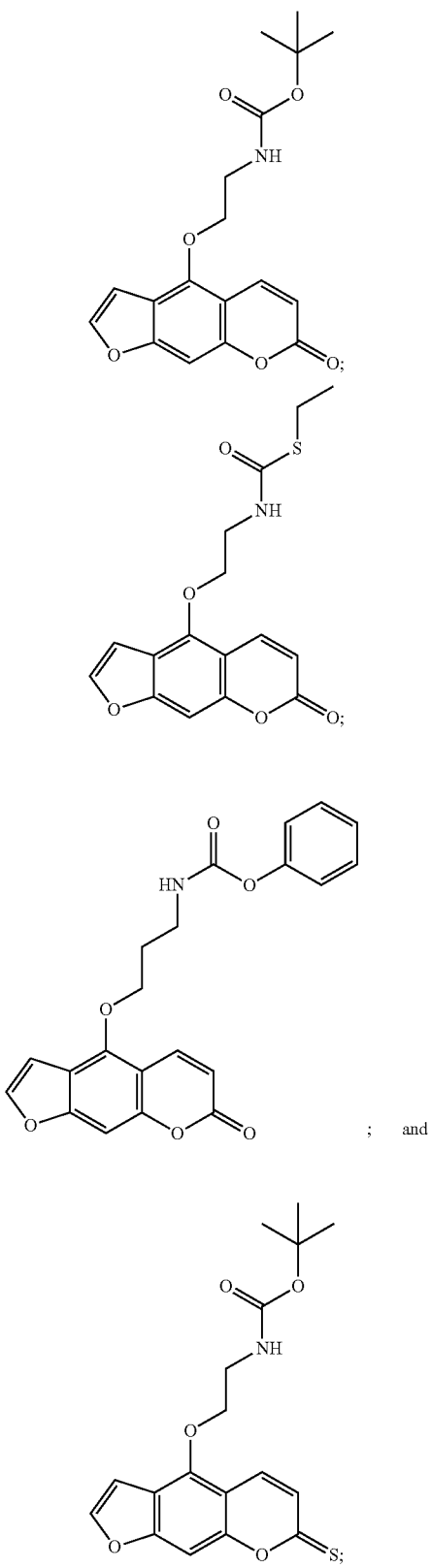

or a pharmaceutically acceptable salt thereof.

In another general aspect, the present application provides compound of Formula (II):

(II)

or a pharmaceutically acceptable salt thereof, wherein:

$X^1$ and $X^2$ are independently selected from O and S;

L is selected from $C_{1-6}$ alkylene, $C_{2-6}$ alkenylene and $C_{2-6}$ alkynylene, each of which is optionally substituted with 1, 2, or 3 substituents independently selected from $R^a$;

ring A is 4-10 membered heterocycloalkyl, optionally substituted with 1, 2, or 3 substituents independently selected from $R^a$;

W is selected from O, S and $NR^1$;

$R^1$ is selected from H, CN, $C_{1-3}$ alkyl, $C_{1-3}$ haloalkyl, $C_{2-4}$ alkenyl and $C_{2-4}$ alkynyl; and $R^2$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-14 membered heteroaryl, and 4-10 membered heterocycloalkyl, each of which is optionally substituted with 1, 2, or 3 substituents independently selected from $R^a$.

each $R^a$ is independently selected from OH, $NO_2$, CN, halo, $C_{1-3}$ alkoxy, $C_{1-3}$ haloalkoxy, $NH_2$, $C_{1-3}$ alkylamino and di($C_{1-3}$ alkyl)amino.

In some embodiments, $X^1$ is O.

In some embodiments, L is $C_{1-3}$ alkylene.

In some embodiments, L is selected from methylene, 1,1-ethylene, 1,2-ethylene, 1,3-propylene, and 2,2-propylene.

In some embodiments, L is methylene.

In some embodiments, ring A is a 4-6-membered heterocycloalkyl, optionally substituted with 1, 2, or 3 substituents independently selected from $R^a$.

In some embodiments, ring A is selected from azetidinyl, pyrrolidinyl, piperidinyl, piperazinyl, oxazolidinyl and morpholinyl, each of which is optionally substituted with 1, 2, or 3 substituents independently selected from $R^a$.

In some embodiments, ring A is selected from dihydroazetyl, dihydropyrrolyl, dihydropyrazinyl, tetrahydropyrazinyl, oxazinyl, dihydrooxazinyl, dihydropyridinyl, and tetrahydropyridinyl, each of which is optionally substituted with 1, 2, or 3 substituents independently selected from $R^a$.

In some embodiments, ring A is selected form azetidinyl, pyrrolidinyl, and piperidinyl.

In some embodiments, ring A is azetidin-3-yl.

In some embodiments, W is O.

In some embodiments, $X^2$ is O.

In some embodiments, $R^2$ is selected from $C_{1-6}$ alkyl, $C_{1-6}$ haloalkyl, $C_{3-10}$ cycloalkyl and $C_{6-10}$ aryl, each of which is optionally substituted with 1, 2, or 3 substituents independently selected from $R^a$.

In some embodiments, $R^a$ is selected from OH, $NO_2$, CN, halo, $C_{1-3}$ alkoxy and $C_{1-3}$ haloalkoxy.

In some embodiments, $R^2$ is $C_{1-6}$ alkyl.

In some embodiments, $R^2$ is tert-butyl.

In some embodiments:

$X^1$ is O;

L is $C_{1-3}$ alkylene;

ring A is a 4-6-memebered heterocycloalkyl, optionally substituted with 1, 2, or 3 substituents independently selected from $R^a$;

W is O;

$X^2$ is O;

$R^2$ is selected from $C_{1-6}$ alkyl, $C_{1-6}$ haloalkyl, $C_{3-10}$ cycloalkyl and $C_{6-10}$ aryl, each of which is optionally substituted with 1, 2, or 3 substituents independently selected from $R^a$; and each $R^a$ is in dependently selected from OH, $NO_2$, CN, halo, $C_{1-3}$ alkoxy and $C_{1-3}$ haloalkoxy.

In some embodiments:

$X^1$ is O;

L is $C_{1-3}$ alkylene;

ring A is azetidinyl;

W is O;

$X^2$ is O; and $R^2$ is $C_{1-6}$ alkyl.

In some embodiments, the compound of Formula (II) has Formula (IIa):

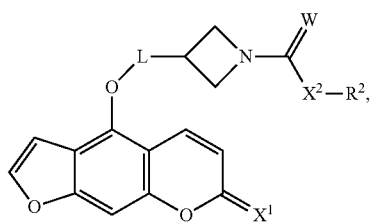

(IIa)

or a pharmaceutically acceptable salt thereof.

In some embodiments, the compound of Formula (II) is:

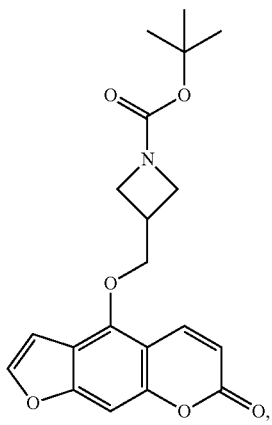 [SMILES: CC(C)(C)OC(=O)N1CC(COc2c3ccoc3cc3oc(=O)ccc23)C1]

or a pharmaceutically acceptable salt thereof.

In yet another general aspect, the present application provides a compound of Formula (III):

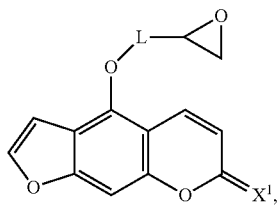

(III)

or a pharmaceutically acceptable salt thereof, wherein:

$X^1$ is selected from O and S; and

L is $C_{1-6}$ alkylene, optionally substituted with 1, 2, or 3 substituents independently selected from OH, $NO_2$, CN, halo, $C_{1-3}$ alkoxy, $C_{1-3}$ haloalkoxy, $NH_2$, $C_{1-3}$ alkylamino and di($C_{1-3}$ alkyl)amino.

In some embodiments, $X^1$ is O.

In some embodiments, L is $C_{1-3}$ alkylene, optionally substituted with 1, 2, or 3 substituents independently selected from OH, $NO_2$, CN, halo, $C_{1-3}$ alkoxy, and $C_{1-3}$ haloalkoxy.

In some embodiments, L is $C_{1-3}$ alkylene.

In some embodiments, L is selected from methylene and ethylene.

In some embodiments, L is methylene.

In some embodiments, the compound of Formula (III) is:

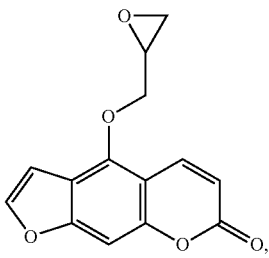 [SMILES: O=c1ccc2c(OCC3CO3)c3ccoc3cc2o1]

or a pharmaceutically acceptable salt thereof.

In yet another general aspect, the present application provides a pharmaceutical composition comprising any one of the compounds described herein, or a pharmaceutically acceptable salt thereof, and a pharmaceutically acceptable carrier.

In yet another general aspect, the present application provides a method of treating or preventing cardiotoxicity induced by an anthracycline chemotherapeutic agent in a subject, the method comprising administering to the subject in need thereof a therapeutically effective amount of any one of the compounds described herein, or a pharmaceutically acceptable salt thereof, or a pharmaceutical composition comprising the compound.

In some embodiments, administration of the compound to the subject does not interfere with ability of the anthracycline chemotherapeutic agent to kill a tumor cell.

In yet another general aspect, the present application provides a method of inhibiting induction of a Cytochrome P450 family 1 (CYP1) enzyme in a cardiomyocyte, the method comprising contacting the cardiomyocyte with any one of the compounds described herein, or a pharmaceutically acceptable salt thereof.

In some embodiments, the Cytochrome P450 family 1 (CYP1) enzyme is induced by contacting the cardiomyocyte with an anthracycline chemotherapeutic agent.

In yet another general aspect, the present application provides a method of inhibiting a Cytochrome P450 family 1 (CYP1) enzyme in a cardiomyocyte, the method comprising contacting the cardiomyocyte with any one of the compounds described herein, or a pharmaceutically acceptable salt thereof.

In some embodiments, the Cytochrome P450 family 1 (CYP1) enzyme is selected from CYP1A and CYP1B1.

In yet another general aspect, the present application provides a method of inhibiting apoptosis induced by an anthracycline chemotherapeutic agent in a cardiomyocyte, the method comprising contacting the cardiomyocyte with any one of the compounds described herein, or a pharmaceutically acceptable salt thereof.

In yet another general aspect, the present application provides a method of modulating an aryl hydrocarbon receptor (AHR) in a cardiomyocyte, the method comprising contacting the cardiomyocyte with any one of the compounds described herein, or a pharmaceutically acceptable salt thereof.

In some embodiments, the modulating comprises antagonizing the aryl hydrocarbon receptor (AHR) in a cardiomyocyte.

In some embodiments, the aryl hydrocarbon receptor (AHR) is activated by contacting the cardiomyocyte with an anthracycline chemotherapeutic agent.

In some embodiments, the cardiomyocyte is contacted in vitro.

In some embodiments, the cardiomyocyte is contacted in vivo.

In some embodiments, the cardiomyocyte is contacted ex vivo.

In some embodiments, the anthracycline chemotherapeutic agent is doxorubicin, or a pharmaceutically acceptable salt thereof.

In yet another general aspect, the present application provides a method of treating cancer in a subject, the method comprising administering to the subject in need thereof a therapeutically effective amount of an anthracycline chemotherapeutic agent, or a pharmaceutically acceptable salt thereof, and a therapeutically effective amount of any one of the compounds described herein, or a pharmaceutically acceptable salt thereof.

In some embodiments, the cancer is selected from breast cancer, leukemia, lymphoma, and sarcoma.

In some embodiments, the anthracycline chemotherapeutic agent, or a pharmaceutically acceptable salt thereof, and the compound, or a pharmaceutically acceptable salt thereof, are administered simultaneously.

In some embodiments, the anthracycline chemotherapeutic agent, or a pharmaceutically acceptable salt thereof, and the compound, or a pharmaceutically acceptable salt thereof, are administered consecutively.

In some embodiments, the anthracycline chemotherapeutic agent, or a pharmaceutically acceptable salt thereof, is administered to the subject prior to the administration of the compound, or a pharmaceutically acceptable salt thereof.

In some embodiments, the compound, or a pharmaceutically acceptable salt thereof, is administered to the subject prior to administration of the anthracycline chemotherapeutic agent, or a pharmaceutically acceptable salt thereof.

In some embodiments, the subject does not develop a cardiotoxicity or a cardiomyopathy associated with the administration of the anthracycline chemotherapeutic agent.

In some embodiments, the cardiotoxicity or the cardiomyopathy is characterized by pericardial edema, impaired cardiac contractility, or decreased blood flow through the vasculature.

In some embodiments, the anthracycline chemotherapeutic agent is doxorubicin, or a pharmaceutically acceptable salt thereof.

In yet another general aspect, the present application provides a pharmaceutical composition comprising a compound of formula:

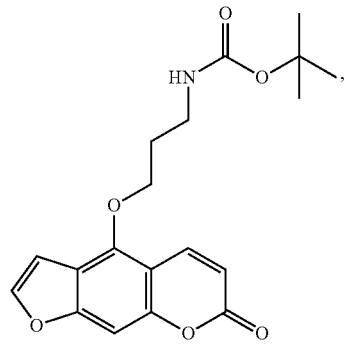

or a pharmaceutically acceptable salt thereof, and a pharmaceutically acceptable carrier.

In yet another general aspect, the present application provides a method of treating or preventing cardiotoxicity induced by an anthracycline chemotherapeutic agent in a subject, the method comprising administering to the subject in need thereof a therapeutically effective amount of a compound of formula:

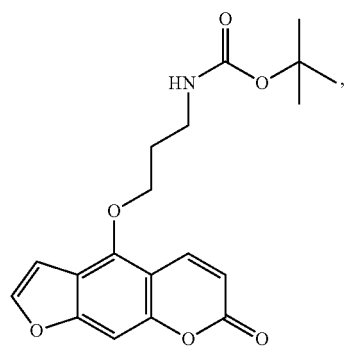 [SMILES: CC(C)(C)OC(=O)NCCCOc1c2ccoc2cc2oc(=O)ccc12]

or a pharmaceutically acceptable salt thereof, or a pharmaceutical composition comprising the compound.

In some embodiments, administration of the compound of formula:

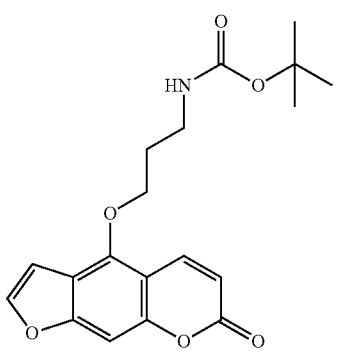 [SMILES: CC(C)(C)OC(=O)NCCCOc1c2ccoc2cc2oc(=O)ccc12]

to the subject does not interfere with ability of the anthracycline chemotherapeutic agent to kill a tumor cell.

In yet another general aspect, the present application provides a method of inhibiting induction of a Cytochrome P450 family 1 (CYP1) enzyme in a cardiomyocyte, the method comprising contacting the cardiomyocyte with a compound of formula:

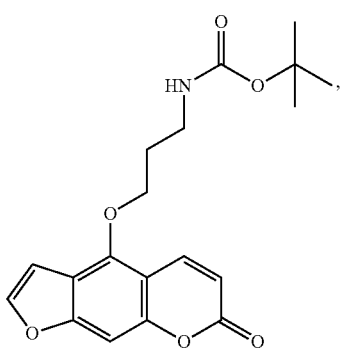 [SMILES: CC(C)(C)OC(=O)NCCCOc1c2ccoc2cc2oc(=O)ccc12]

or a pharmaceutically acceptable salt thereof.

In some embodiments, the Cytochrome P450 family 1 (CYP1) enzyme is induced by contacting the cardiomyocyte with an anthracycline chemotherapeutic agent.

In yet another general aspect, the present application provides a method of inhibiting a Cytochrome P450 family 1 (CYP1) enzyme in a cardiomyocyte, the method comprising contacting the cardiomyocyte with a compound of formula:

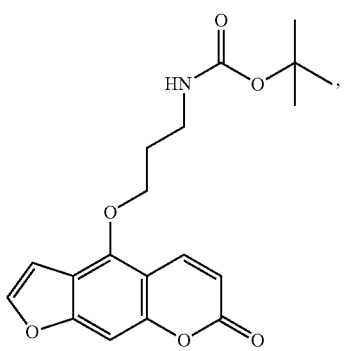 [SMILES: CC(C)(C)OC(=O)NCCCOc1c2ccoc2cc2oc(=O)ccc12]

or a pharmaceutically acceptable salt thereof.

In some embodiments, the Cytochrome P450 family 1 (CYP1) enzyme is selected from CYP1A and CYP1B1.

In yet another general aspect, the present application provides a method of inhibiting apoptosis induced by an anthracycline chemotherapeutic agent in a cardiomyocyte, the method comprising contacting the cardiomyocyte with a compound of formula:

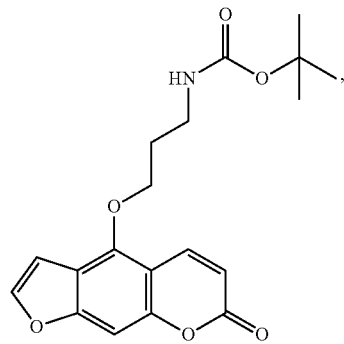

or a pharmaceutically acceptable salt thereof.

In yet another general aspect, the present application provides a method of modulating an aryl hydrocarbon receptor (AHR) in a cardiomyocyte, the method comprising contacting the cardiomyocyte with a compound of formula:

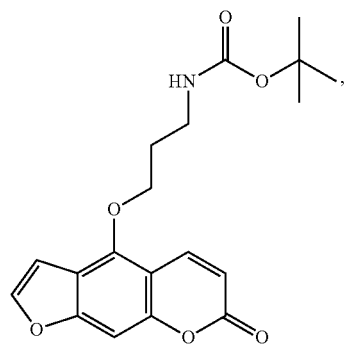 [SMILES: CC(C)(C)OC(=O)NCCCOc1c2ccoc2cc2oc(=O)ccc12]

or a pharmaceutically acceptable salt thereof.

In some embodiments, the modulating comprises antagonizing the aryl hydrocarbon receptor (AHR) in a cardiomyocyte.

In some embodiments, the aryl hydrocarbon receptor (AHR) is activated by contacting the cardiomyocyte with an anthracycline chemotherapeutic agent.

In some embodiments, the cardiomyocyte is contacted in vitro.

In some embodiments, the cardiomyocyte is contacted in vivo.

In some embodiments, the cardiomyocyte is contacted ex vivo.

In some embodiments, the anthracycline chemotherapeutic agent is doxorubicin, or a pharmaceutically acceptable salt thereof.

In yet another general aspect, the present application provides a method of treating cancer in a subject, the method comprising administering to the subject in need thereof a therapeutically effective amount of an anthracycline chemotherapeutic agent, or a pharmaceutically acceptable salt thereof, and a therapeutically effective amount of a compound of formula:

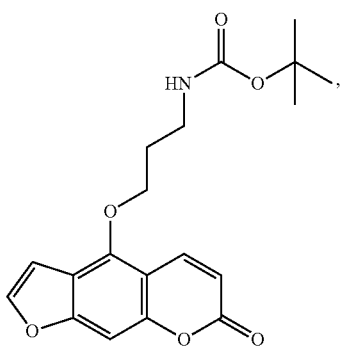 [SMILES: CC(C)(C)OC(=O)NCCCOc1c2ccoc2cc2oc(=O)ccc12]

or a pharmaceutically acceptable salt thereof.

In some embodiments, the cancer is selected from breast cancer, leukemia, lymphoma, and sarcoma.

In some embodiments, the anthracycline chemotherapeutic agent, or a pharmaceutically acceptable salt thereof, and the compound formula:

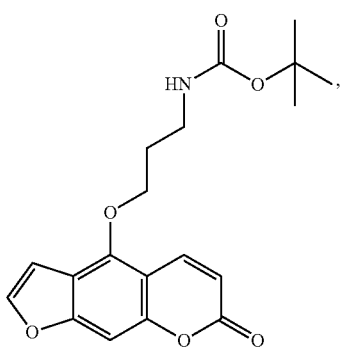 [SMILES: CC(C)(C)OC(=O)NCCCOc1c2ccoc2cc2oc(=O)ccc12]

or a pharmaceutically acceptable salt thereof, are administered simultaneously.

In some embodiments, the anthracycline chemotherapeutic agent, or a pharmaceutically acceptable salt thereof, and the compound of formula:

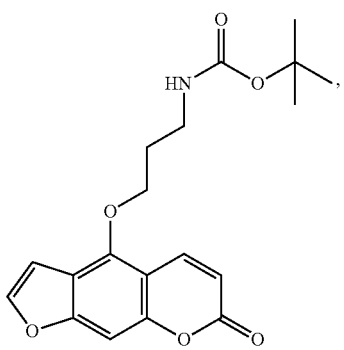 [SMILES: CC(C)(C)OC(=O)NCCCOc1c2ccoc2cc2oc(=O)ccc12]

or a pharmaceutically acceptable salt thereof, are administered consecutively.

In some embodiments, the anthracycline chemotherapeutic agent, or a pharmaceutically acceptable salt thereof, is administered to the subject prior to the administration of the compound of formula:

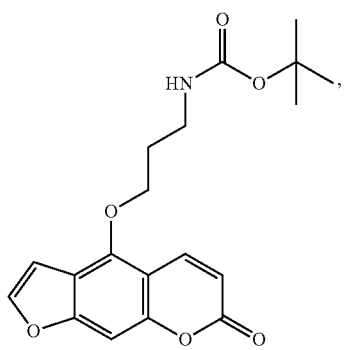

or a pharmaceutically acceptable salt thereof.

In some embodiments, the compound of formula:

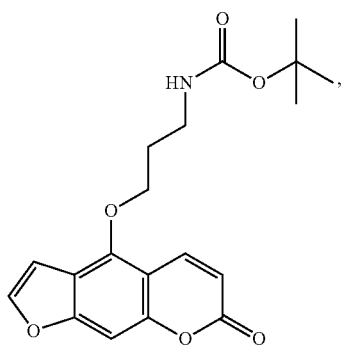 [SMILES: CC(C)(C)OC(=O)NCCCOc1c2ccoc2cc2oc(=O)ccc12]

or a pharmaceutically acceptable salt thereof, is administered to the subject prior to administration of the anthracycline chemotherapeutic agent, or a pharmaceutically acceptable salt thereof.

In some embodiments, the subject does not develop a cardiotoxicity or a cardiomyopathy associated with the administration of the anthracycline chemotherapeutic agent.

In some embodiments, the cardiotoxicity or the cardiomyopathy is characterized by pericardial edema, impaired cardiac contractility, or decreased blood flow through the vasculature.

In some embodiments, the anthracycline chemotherapeutic agent is doxorubicin, or a pharmaceutically acceptable salt thereof.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

Figure 1A:
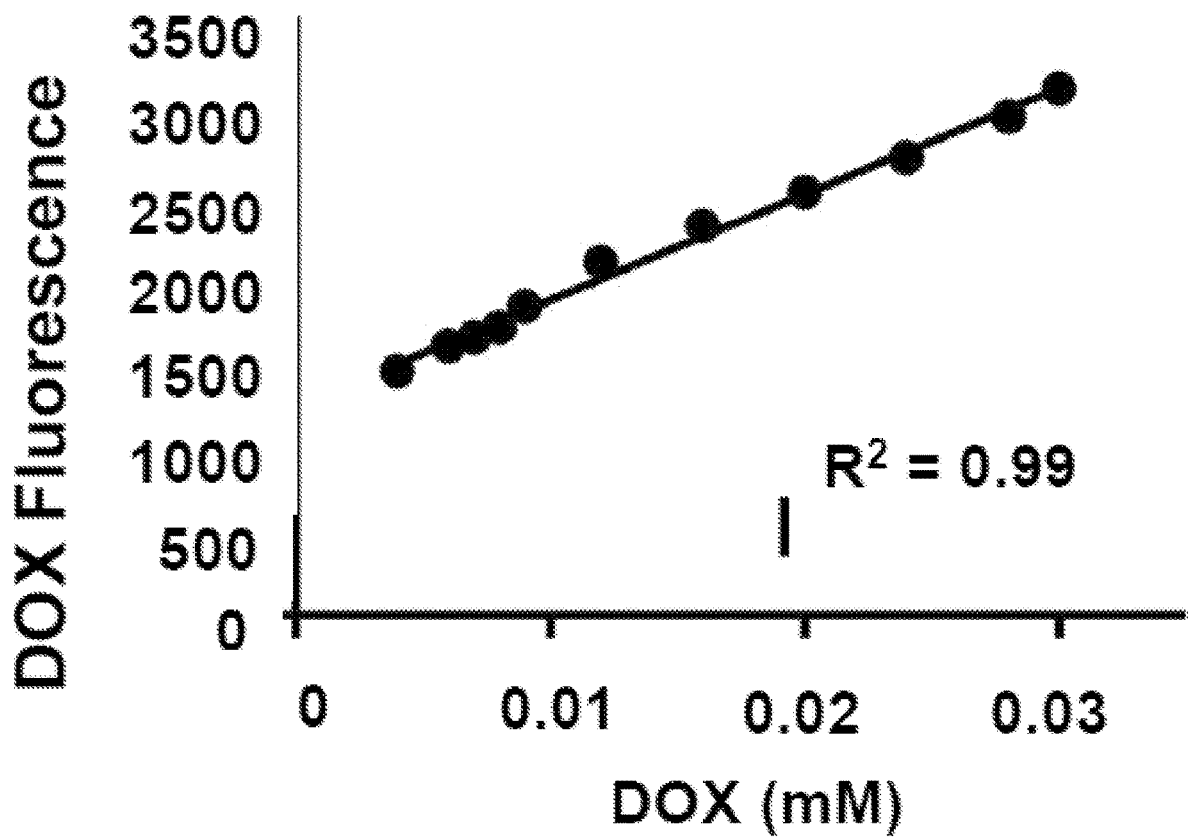
FIG. 1A is a line plot showing that DOX fluorescence in a phantom calibration study increased linearly with increasing concentration.

Although the mechanisms leading to the development of DOX cardiotoxicity have not been clearly defined, oxidative stress and mitochondrial dysfunction have been implicated as key mediators (Suliman et al., 2007; Wallace, 2003; Zhou et al., 2001). Currently, dexrazoxane is the only compound approved by the FDA to prevent DOX-induced cardiotoxicity in patients. Dexrazoxane has been proposed to chelate intracellular iron, block iron-assisted oxidative radical production, and inhibit topoisomerase 2β (Hasinoff and Herman, 2007; Ichikawa et al., 2014; Lyu et al., 2007; Zhang et al., 2012). Preclinical studies in mice suggested that a dose ratio of between 10:1 and 20:1 (dexrazoxane:DOX) was required to significantly reduce the incidence of DOX-induced cardiomyopathy (Imondi, 1998; Imondi et al., 1996). Accordingly, dexrazoxane is typically prescribed to patients undergoing treatment with DOX at a dose ratio of 10:1. Although recent studies have found dexrazoxane to be a safe adjunct to DOX therapy (Asselin et al., 2016; Seif et al., 2015), many clinicians choose not to administer dexrazoxane to patients given concerns that it may interfere with DOX's ability to kill tumor cells (Swain et al., 1997) and/or induce secondary malignancies (Tebbi et al., 2007).

Based on the concern for precipitating cardiotoxicity, patients may not receive the anthracycline dose necessary for optimal treatment of their cancer. The present application describes, inter alia, selective cardioprotective compounds that can be administered to patients at the time of doxorubicin therapy, without interfering with doxorubicin's ability to kill cancer cells and/or inducing secondary malignancies. The ci cardioprotective compounds described herein may also enhance doxorubicin's antitumor effect. Methods of making and using the cardioprotective compounds are also described.

Definitions

At various places in the present specification, substituents of compounds of the present application are disclosed in groups or in ranges. It is specifically intended that various embodiments of the present application include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

As used herein, the term "about" means "approximately" (e.g., plus or minus approximately 10% of the indicated value).

As used herein, the term "compound" as used herein is meant to include all stereoisomers, geometric isomers, tautomers, and isotopes of the structures named or depicted. Compounds herein identified by name or structure as one particular tautomeric form are intended to include other tautomeric forms unless otherwise specified.

As used herein, the term "tautomer" refers to compounds which are capable of existing in a state of equilibrium between two isomeric forms. Such compounds may differ in the bond connecting two atoms or groups and the position of these atoms or groups in the compound.

As used herein, the term "isomer" refers to structural, geometric and stereo isomers. As the compound of the present application may have one or more chiral centers, it is capable of existing in enantiomeric forms.

Throughout the definitions, the term "$C_{n-m}$" indicates a range which includes the endpoints, wherein n and m are integers and indicate the number of carbon atoms. Examples include $C_{1-4}$, $C_{1-6}$, and the like.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain (linear) or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkylene" means a bivalent saturated branched, or straight chain (linear) chemical group containing only carbon and hydrogen atoms, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms. The term "$C_{n-m}$ alkenylene" refers to a divalent alkenyl group.

As used herein, "$C_{n-m}$ alkynyl" means a straight or branched chain chemical group containing only carbon and hydrogen, containing n to m carbon atoms and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms). The term "$C_{n-m}$ alkynylene" refers to a divalent alkynyl group.

As used herein, the term "$C_{n-m}$ alkoxy", employed alone or in combination with other terms, refers to a group of formula —O—$C_{n-m}$ alkyl, wherein the alkyl group contains n to m carbon atoms. Exemplary alkoxy groups include, but are not limited to, methoxy, ethoxy, propoxy (e.g., n-propoxy and isopropoxy), butoxy (e.g., n-butoxy and tert-butoxy), and the like. In some embodiments, the alkoxy group has 1 to 6, 1 to 4, or 1 to 3 carbon atoms.

As used herein, "halo" refers to a halogen atom such as F, Cl, Br, or I. In some embodiments, a halo is F, Cl, or Br. In other embodiments, halo is F, Cl, or I. In other embodiments, halo is F, I, or Br.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "di $C_{n-m}$ alkylamino" refers to a group of formula —N(alkyl)$_2$, wherein each alkyl group independently has n to m carbon atoms. In some embodiments, each alkyl group has 1 to 6, 1 to 4, or 1 to 3 carbon atoms. Examples of dialkylamino groups include, but are not limited to, N,N-methylehtylamino, N,N-diethylamino, N,N-propylethylamino, N,N-butylisopropylamino, and the like.

As used herein, "cycloalkyl" refers to non-aromatic saturated or unsaturated cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the non-aromatic cyclic hydrocarbon, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, or 12 ring-forming atoms. In some embodiments, the cycloalkyl is a 3-12 membered monocyclic or bicyclic cycloalkyl. In some embodiments, the cycloalkyl is a $C_{3-7}$ monocyclic cycloalkyl. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cyclooctyl, cyclooctenyl, and the like. In some embodiments, cycloalkyl is cyclopropyl, cyclobutyl, cyclopentyl, cyclohexyl, cyclooctyl, or cyclooctenyl. In some embodiments, the cycloalkyl is a cyclooctenyl ring fused with 1 or 2 benzene rings. In some embodiments, the cycloalkyl is a 3-8 membered or 3-7 membered monocyclic cycloalkyl group (e.g., $C_{3-8}$ or $C_{3-7}$ cycloalkyl). In some embodiments, the cycloalkyl is a 8-12-membered bicyclic cycloalkyl. In some embodiments, the cycloalkyl is a 8-16-membered bicyclic or tricyclic cycloalkyl (e.g., $C_{8-16}$ cycloalkyl). In some embodiments, the cycloalkyl is unsaturated cyclic hydrocarbon group (i.e., the cycloalkyl contains at least one double bond).

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 membered monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered heteroaryls are pyridyl, pyrazinyl, pyrimidinyl, triazinyl and pyridazinyl. The term "heteroarylene" refers to a divalent heteroaryl linking group.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl. The term "arylene" refers to a divalent aryl linking group.

As used herein, "heterocycloalkyl" or "aliphatic heterocycle" refers to non-aromatic saturated or unsaturated monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups.

Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido groups (e.g., C(O), S(O), C(S), or S(O)2, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. In some embodiments, the heterocycloalkyl group is unsaturated (i.e., the heterocycloalkyl contains at least one double bond). Also included in the definition of heterocycloalkyl are moieties that have one or more aromatic rings fused (i.e., having a bond in common with) to the non-aromatic heterocycle, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. In some embodiments, the heterocycloalkyl is a 8-12-membered heterocycloalkyl (e.g., bicyclic heterocycloalkyl). In some embodiments, the heterocycloalkyl is a 8-16-membered heterocycloalkyl (e.g., bicyclic or tricyclic heterocycloalkyl). In some embodiments, the 8-12 membered bicyclic heterocycloalkyl is a 8-12 membered fused heterocycloalkylaryl group or a 8-12 membered fused heterocycloalkylheteroaryl group. In some embodiments, the heterocycloalkyl is a 9-12 membered bicyclic heterocycloalkyl. In some embodiments, the 9-10 membered bicyclic heterocycloalkyl is a 9-10 membered fused heterocycloalkylaryl group or a 9-10 membered fused heterocycloalkylheteroaryl group. The term "heterocycloalkylene" refers to a divalent heterocycloalkyl linking group.

The terms "pharmaceutical" and "pharmaceutically acceptable" are employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the terms "maximum safe dosage", "maximum tolerated dosage" or "maximum recommended therapeutic dosage" indicate the highest amount of a therapeutic agent that can be given that minimizes complications or side effects to a patient while maintaining its efficacy as a treatment. Such a dose can be adjusted to consider the patient's overall heath and any extenuating factors that could hamper the patient's recovery.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

Therapeutic Compounds

The present application provides, inter alia, a compound of Formula (I):

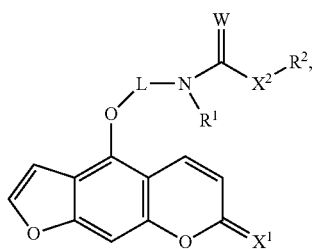

or a pharmaceutically acceptable salt thereof, wherein:
$X^1$ and $X^2$ are independently selected from O and S;
W is selected from O, S and $NR^1$;
L is selected from $C_{1-6}$ alkylene, $C_{2-6}$ alkenylene and $C_{2-6}$ alkynylene, each of which is optionally substituted with 1, 2, or 3 substituents independently selected from $R^a$;
$R^1$ is selected from H, $C_{1-3}$ alkyl, $C_{1-3}$ haloalkyl, $C_{2-4}$ alkenyl and $C_{2-4}$ alkynyl; and
$R^2$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-14 membered heteroaryl, and 4-10 membered heterocycloalkyl, each of which is optionally substituted with 1, 2, or 3 substituents independently selected from $R^a$; and
each $R^a$ is independently selected from OH, $NO_2$, CN, halo, $C_{1-3}$ alkoxy, $C_{1-3}$ haloalkoxy, $NH_2$, $C_{1-3}$ alkylamino and di($C_{1-3}$ alkyl)amino.

In some embodiments of Formula (I), $X^1$ is selected form O and S. In some embodiments of Formula (I), $X^1$ is O. In other embodiments of Formula (I), $X^1$ is S.

In some embodiments of Formula (I), $X^2$ is selected form O and S. In some embodiments of Formula (I), $X^2$ is O. In other embodiments of Formula (I), $X^2$ is S.

In some embodiments of Formula (I), W is selected from O and S. In some embodiments of Formula (I), W is O. In other embodiments, W is S.

In some embodiments of Formula (I), W is $NR^1$.

In some embodiments of Formula (I), $R^1$ is selected form H, $C_{1-3}$ alkyl and $C_{1-3}$ haloalkyl. In some embodiments of Formula (I), $R^1$ is CN. In some embodiments of Formula (I), $R^1$ is selected form H and $C_{1-3}$ alkyl. In some embodiments of Formula (I), $R^1$ is H. In some embodiments of Formula (I), $R^1$ is $C_{1-4}$ alkyl. In some embodiments of Formula (I), $R^1$ is selected form methyl, ethyl, propyl, isopropyl, and tert-butyl.

In some embodiments of Formula (I), W is NH. In some embodiments of Formula (I), W is N(CN). In some embodiments of Formula (I), W is N($C_{1-4}$ alkyl). In some embodiments of Formula (I), W is N(tert-butyl).

In some embodiments of Formula (I), L is $C_{1-6}$ alkylene, optionally substituted with 1 or 2 substituents independently selected from $R^a$. In some embodiments of Formula (I), L is $C_{1-4}$ alkylene, optionally substituted with $R^a$.

In some embodiments of Formula (I), L is $C_{2-6}$ alkenylene, optionally substituted with 1 or 2 substituents independently selected from $R^a$.

In some embodiments of Formula (I), L is $C_{2-6}$ alkynylene, optionally substituted with 1 or 2 substituents independently selected from $R^a$.

In some embodiments of Formula (I), L is $C_{1-6}$ alkylene. In some embodiments of Formula (I), L is $C_{1-4}$ alkylene. In some embodiments of Formula (I), L is $C_{2-4}$ alkylene. In some embodiments of Formula (I), L is $C_{2-6}$ alkenylene. In some embodiments of Formula (I), L is $C_{2-4}$ alkenylene. In some embodiments of Formula (I), L is $C_{2-6}$ alkynylene. In some embodiments of Formula (I), L is $C_{2-4}$ alkynylene.

In some embodiments of Formula (I), L is a linear (straight chain) $C_{1-6}$ alkylene. In some aspects of these embodiments, L is unsubstituted. In other aspects of these embodiments, L is substituted with 1 or 2 substituents independently selected form $R^a$.

In some embodiments of Formula (I), L is a branched unsubstituted $C_{1-6}$ alkylene.

In some embodiments of Formula (I), L is methylene. In some aspects of these embodiments, L is unsubstituted. In other aspects of these embodiments, L is methylene optionally substituted with $R^a$.

In some embodiments of Formula (I), L is ethylene. In some aspects of these embodiments, L is 1,1-ethylene. In other aspects of these embodiments, L is 1,2-ethylene. In some embodiments of Formula (I), L is ethylene optionally substituted with $R^a$.

In some embodiments of Formula (I), L is propylene. In some aspects of these embodiments, L is 1,3-propylene. In other aspects of these embodiments, L is 1,2-propylene. In some embodiments of Formula (I), L is propylene optionally substituted with $R^a$. In some embodiments of Formula (I), L a $C_{1-6}$ alkylene other than 1,3-propylene.

In some embodiments of Formula (I), L is selected from methylene, 1,2-ethylene, 1,3-propylene, 1,4-butylene, 1,5-pentylene and 1,6-hexylene. In some embodiments of Formula (I), L is selected from methylene, 1,2-ethylene and 1,3-propylene. In some embodiments of Formula (I), L is selected from methylene and 1,2-ethylene.

In some embodiments of Formula (I), $R^2$ is selected from $C_{1-6}$ alkyl, $C_{1-6}$ haloalkyl, $C_{3-10}$ cycloalkyl and $C_{6-10}$ aryl, each of which is optionally substituted with 1, 2, or 3 substituents independently selected from $R^a$.

In some embodiments of Formula (I), $R^2$ is 5-14 membered heteroaryl, optionally substituted with 1 or 2 substituents independently selected from $R^a$. For example, $R^2$ is selected form pyridinyl, pyrimidinyl, pyrazolyl, imidazolyl, and quinolinyl, each of which is optionally substituted with 1 or 2 independently selected $R^a$.

In some embodiments of Formula (I), $R^2$ is 4-10 membered heterocycloalkyl, optionally substituted with 1 or 2 substituents independently selected from $R^a$. For example, $R^2$ is selected from azetidinyl, pyrrolidinyl, piperidinyl, piperazinyl, oxazolidinyl and morpholinyl, each of which is optionally substituted with 1 or 2 substituents independently selected from $R^a$.

In some embodiments of Formula (I), $R^2$ is $C_{3-10}$ cycloalkyl, optionally substituted with 1 or 2 substituents independently selected from $R^a$. For example, $R^2$ is selected form cyclopropyl, cyclobutyl, cyclopentyl, cyclohexyl, and cyclopentyl, each of which is optionally substituted with 1 or 2 substituents independently selected from $R^a$.

In some embodiments of Formula (I), $R^2$ is selected from $C_{1-6}$ alkyl and $C_{6-10}$ aryl, each of which is optionally substituted with 1 or 2 substituents independently selected from $R^a$. In some embodiments of Formula (I), $R^2$ is selected from $C_{1-6}$ alkyl and $C_{6-10}$ aryl.

In some embodiments of Formula (I), $R^2$ is $C_{6-10}$ aryl, optionally substituted with 1 or 2 substituents independently selected from $R^a$. In some embodiments of Formula (I), $R^2$ is phenyl, optionally substituted with 1 or 2 substituents independently selected from $R^a$. In some embodiments of Formula (I), $R^2$ is phenyl.

In some embodiments of Formula (I), $R^2$ is $C_{1-6}$ alkyl. In some embodiments of Formula (I), $R^2$ is $C_{1-4}$ alkyl. In some embodiments of Formula (I), $R^2$ is $C_{1-6}$ alkyl optionally substituted with 1 or 2 substituents independently selected from $R^a$. In some embodiments of Formula (I), $R^2$ is methyl, ethyl, propyl, isopropyl, or tert-butyl. In some embodiments of Formula (I), $R^2$ is ethyl or tert-butyl.

In some embodiments of Formula (I), $R^2$ is $C_{1-6}$ haloalkyl. In some embodiments of Formula (I), $R^2$ is $C_{1-4}$ haloalkyl. In some embodiments of Formula (I), $R^2$ is $C_{1-3}$ haloalkyl. In some embodiments of Formula (I), $R^2$ is trifluoromethyl, trichloromethyl, 2,2,2-trifluoroethyl, perfluoroethyl, or 1,1,1,3,3,3-hexafluoro-2-(trifluoromethyl)prop-2-yl.

In some embodiments of Formula (I), $R^2$ is selected from ethyl, tert-butyl, and phenyl.

In some embodiments of Formula (I), $R^a$ is selected from OH, $NO_2$, CN, halo, $C_{1-3}$ alkyl, $C_{1-3}$ haloalkyl, $C_{1-3}$ alkoxy, $C_{1-3}$ haloalkoxy, $NH_2$, $C_{1-3}$ alkylamino and di($C_{1-3}$ alkyl)amino.

In some embodiments of Formula (I), $R^a$ is selected from OH, $NO_2$, CN, halo, $C_{1-3}$ alkyl, $C_{1-3}$ haloalkyl, $C_{1-3}$ alkoxy and $C_{1-3}$ haloalkoxy.

In some embodiments of Formula (I), $R^a$ is selected from OH, $NO_2$, CN, halo, $C_{1-3}$ alkoxy and $C_{1-3}$ haloalkoxy.

In some embodiments of Formula (I), $R^a$ is selected from $NH_2$, $C_{1-3}$ alkylamino and di($C_{1-3}$ alkyl)amino.

In some embodiments of Formula (I), $R^a$ is $C_{1-3}$ alkyl.

In some embodiments of Formula (I), $R^a$ is selected from OH, $C_{1-3}$ alkoxy and $C_1$-3 haloalkoxy.

In some embodiments of Formula (I), $R^a$ is selected from $C_{1-3}$ alkyl, OH, $C_{1-3}$ alkoxy, $C_{1-3}$ haloalkoxy, $NH_2$, $C_{1-3}$ alkylamino and di($C_{1-3}$ alkyl)amino.

In some embodiments of Formula (I), $R^a$ is selected from $NO_2$, CN and halo.

In some embodiments of Formula (I):
$X^1$, $X^2$ and W are independently selected from O and S;
L is $C_{1-6}$ alkylene;
$R^1$ is selected form H and $C_{1-3}$ alkyl;
$R^2$ is selected from $C_{1-6}$ alkyl, $C_{1-6}$ haloalkyl, $C_{3-10}$ cycloalkyl and $C_{6-10}$ aryl, each of which is optionally substituted with 1, 2, or 3 substituents independently selected from $R^a$; and
each $R^a$ is independently selected from OH, $NO_2$, CN, halo, $C_{1-3}$ alkoxy and $C_{1-3}$ haloalkoxy.

In some embodiments of Formula (I):
$X^1$ and $X^2$ are independently selected from O and S;
W is O;
L is selected form ethylene and propylene;
$R^1$ is H; and
$R^2$ is selected from $C_{1-6}$ alkyl and $C_{6-10}$ aryl.

In some embodiments, the compound of Formula (I) has formula:

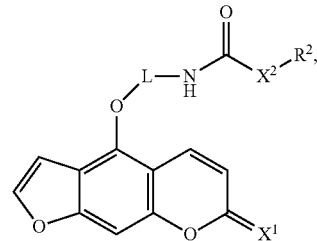

or a pharmaceutically acceptable salt thereof.

In some embodiments, the compound of Formula (I) has formula:

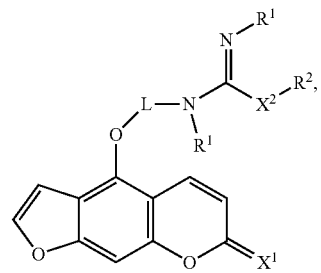

or a pharmaceutically acceptable salt thereof.

In some embodiments, the compound of Formula (I) is selected from:

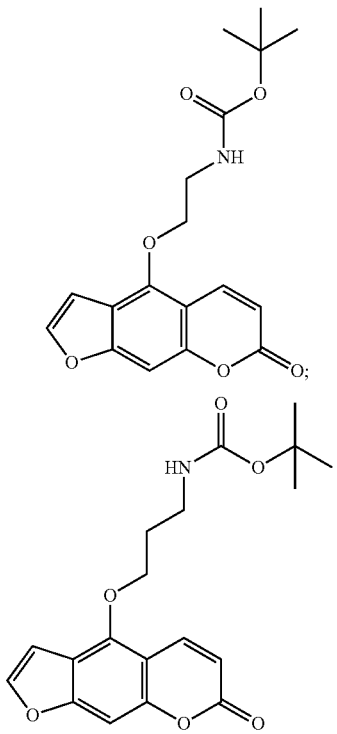

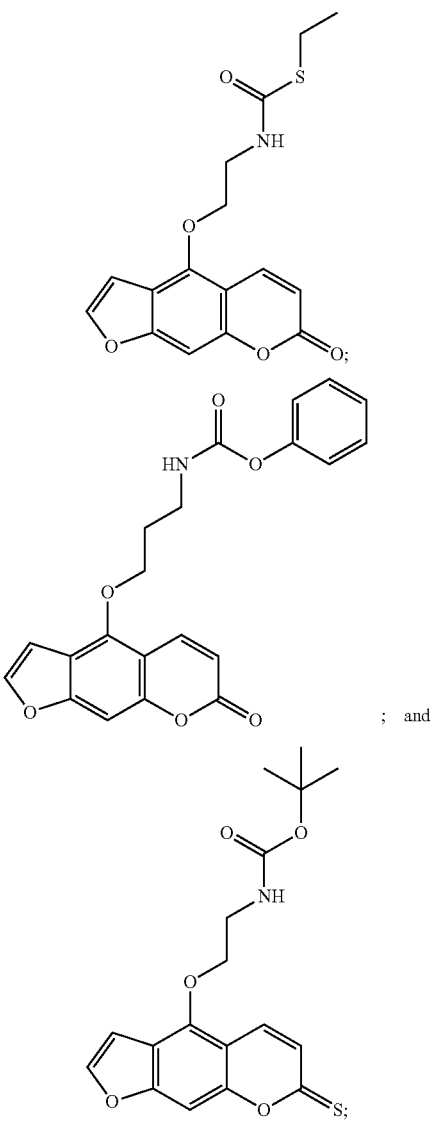

or a pharmaceutically acceptable salt thereof.

In some embodiments, the compound of Formula (I) is not a compound of formula:

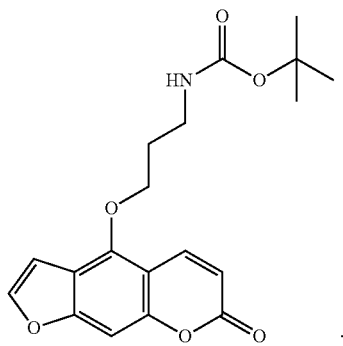 [SMILES: CC(C)(C)OC(=O)NCCCOc1c2ccoc2cc2oc(=O)ccc12]

The present application also provides, inter alia, a compound of Formula (II):

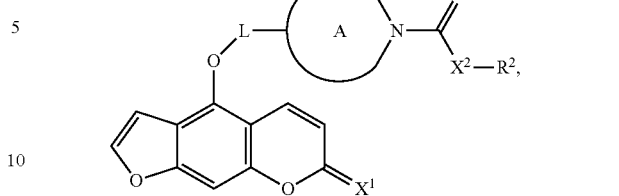

or a pharmaceutically acceptable salt thereof, wherein:
$X^1$ and $X^2$ are independently selected from O and S;
L is selected from $C_{1-6}$ alkylene, $C_{2-6}$ alkenylene and $C_{2-6}$ alkynylene, each of which is optionally substituted with 1, 2, or 3 substituents independently selected from $R^a$;
ring A is 4-10 membered heterocycloalkyl, optionally substituted with 1, 2, or 3 substituents independently selected from $R^a$;
W is selected from O, S and $NR^1$;
$R^1$ is selected from H, CN, $C_{1-3}$ alkyl, $C_{1-3}$ haloalkyl, $C_{2-4}$ alkenyl and $C_{2-4}$ alkynyl;
$R^2$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-14 membered heteroaryl, and 4-10 membered heterocycloalkyl, each of which is optionally substituted with 1, 2, or 3 substituents independently selected from $R^a$; and
each $R^a$ is independently selected from OH, $NO_2$, CN, halo, $C_{1-3}$ alkoxy, $C_{1-3}$ haloalkoxy, $NH_2$, $C_{1-3}$ alkylamino and di($C_{1-3}$ alkyl)amino.

In some embodiments of Formula (II), $X^1$ is selected from O and S. In some embodiments of Formula (II), $X^1$ is O. In some embodiments of Formula (II), $X^1$ is S.

In some embodiments of Formula (II), $X^2$ is selected from O and S. In some embodiments of Formula (II), $X^2$ is O. In some embodiments of Formula (II), $X^2$ is S.

In some embodiments of Formula (II), L is $C_{1-6}$ alkylene, optionally substituted with 1 or 2 substituents independently selected from $R^a$. In some embodiments of Formula (II), L is $C_{1-4}$ alkylene, optionally substituted with $R^a$.

In some embodiments of Formula (II), L is $C_{2-6}$ alkenylene, optionally substituted with 1 or 2 substituents independently selected from $R^a$.

In some embodiments of Formula (II), L is $C_{2-6}$ alkynylene, optionally substituted with 1 or 2 substituents independently selected from $R^a$.

In some embodiments of Formula (II), L is $C_{1-6}$ alkylene. In some embodiments of Formula (II), L is $C_{1-4}$ alkylene. In some embodiments of Formula (II), L is $C_{2-4}$ alkylene. In some embodiments of Formula (II), L is $C_{2-6}$ alkenylene. In some embodiments of Formula (II), L is $C_{2-4}$ alkenylene. In some embodiments of Formula (II), L is $C_{2-6}$ alkynylene. In some embodiments of Formula (II), L is $C_{2-4}$ alkynylene.

In some embodiments of Formula (II), L is a linear (straight chain) $C_{1-6}$ alkylene. In some aspects of these embodiments, L is unsubstituted. In other aspects of these embodiments, L is substituted with 1 or 2 substituents independently selected form $R^a$.

In some embodiments of Formula (II), L is a branched unsubstituted $C_{1-6}$ alkylene.

In some embodiments of Formula (II), L is $C_{1-3}$ alkylene. In some aspects of these embodiments, $C_{1-3}$ alkylene is optionally substituted with 1 or 2 independently selected $R^a$.

In some embodiments of Formula (II), L is methylene. In some aspects of these embodiments, L is unsubstituted. In other aspects of these embodiments, L is methylene optionally substituted with $R^a$.

In some embodiments of Formula (II), L is ethylene. In some aspects of these embodiments, L is 1,1-ethylene. In other aspects of these embodiments, L is 1,2-ethylene. In some embodiments of Formula (II), L is ethylene optionally substituted with $R^a$.

In some embodiments of Formula (II), L is propylene. In some aspects of these embodiments, L is 1,3-propylene. In other aspects of these embodiments, L is 1,2-propylene. In some embodiments of Formula (II), L is propylene optionally substituted with $R^a$.

In some embodiments of Formula (II), L is selected from methylene, 1,2-ethylene, 1,3-propylene, 1,4-butylene, 1,5-pentylene and 1,6-hexylene. In some embodiments of Formula (II), L is selected from methylene, 1,2-ethylene and 1,3-propylene. In some embodiments, L is selected from methylene, 1,1-ethylene, 1,2-ethylene, 1,3-propylene, and 2,2-propylene.

In some embodiments of Formula (II), W is selected from O and S. In some embodiments of Formula (II), W is O. In other embodiments of Formula (II), W is S.

In some embodiments of Formula (II), W is $NR^1$.

In some embodiments of Formula (II), $R^1$ is selected form H, $C_{1-3}$ alkyl and $C_{1-3}$ haloalkyl. In some embodiments of Formula (II), $R^1$ is CN. In some embodiments of Formula (II), $R^1$ is selected form H and alkyl. In some embodiments of Formula (II), $R^1$ is H. In some embodiments of Formula (II), $R^1$ is $C_{1-4}$ alkyl. In some embodiments of Formula (II), $R^1$ is selected form methyl, ethyl, propyl, isopropyl, and tert-butyl.

In some embodiments of Formula (II), W is NH. In some embodiments of Formula (II), W is N(CN). In some embodiments of Formula (II), W is $N(C_{1-4}$ alkyl). In some embodiments of Formula (II), W is N(tert-butyl).

In some embodiments of Formula (II), ring A is 4-10 membered heterocycloalkyl, optionally substituted with 1 or 2 substituents independently selected from $R^a$. In some aspects of these embodiments, ring A is unsubstituted 4-10 membered heterocycloalkyl. In other aspects of these embodiments, ring A is unsubstituted 4-6 membered heterocycloalkyl.

In some embodiments of Formula (II), ring A is a 4-6-membered heterocycloalkyl, optionally substituted with 1, 2, or 3 substituents independently selected from $R^a$.

In some embodiments of Formula (II), ring A is selected from azetidinyl, pyrrolidinyl, piperidinyl, piperazinyl, oxazolidinyl and morpholinyl, each of which is optionally substituted with 1, 2, or 3 substituents independently selected from $R^a$. In some aspects of these embodiments, ring A is an unsubstituted azetidinyl, pyrrolidinyl, piperidinyl, piperazinyl, oxazolidinyl or morpholinyl ring.

In some embodiments of Formula (II), ring A is selected from dihydroazetyl, dihydropyrrolyl, dihydropyrazinyl, tetrahydropyrazinyl, oxazinyl, dihydrooxazinyl, dihydropyridinyl, and tetrahydropyridinyl, each of which is optionally substituted with 1, 2, or 3 substituents independently selected from $R^a$. In some aspects of these embodiments, ring A is an unsubstituted dihydroazetyl, dihydropyrrolyl, dihydropyrazinyl, tetrahydropyrazinyl, oxazinyl, dihydrooxazinyl, dihydropyridinyl, or tetrahydropyridinyl ring.

In some embodiments of Formula (II), ring A is selected from form azetidinyl, pyrrolidinyl, and piperidinyl. In some aspects of these embodiments, each of the azetidinyl, pyrrolidinyl, and piperidinyl rings is optionally substituted with 1 or 2 independently selected $R^a$.

In some embodiments of Formula (II), ring A is a morpholinyl of Formula:

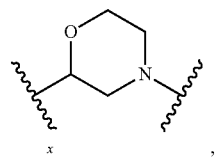 [SMILES: *C1CN(*)CCO1]

wherein x designates a point of attachment of ring A to L.

In some embodiments of Formula (II), ring A is a tetrahydropyridinyl of Formula:

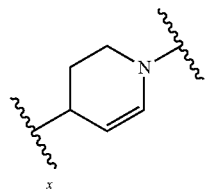

wherein x designates a point of attachment of ring A to L.

In some embodiments of Formula (II), ring A is a piperidinyl of Formula:

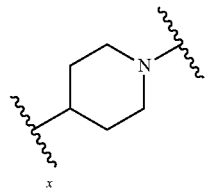

wherein x designates a point of attachment of ring A to L.

In some embodiments of Formula (II), ring A is a pyrrolidinyl of Formula:

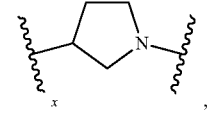

wherein x designates a point of attachment of ring A to L.

In some embodiments of Formula (II), ring A is azetidin-3-yl.

In some embodiments of Formula (II), $R^2$ is selected from $C_{1-6}$ alkyl, $C_{1-6}$ haloalkyl, $C_{3-10}$ cycloalkyl and $C_{6-10}$ aryl, each of which is optionally substituted with 1, 2, or 3 substituents independently selected from $R^a$.

In some embodiments of Formula (II), $R^2$ is 5-14 membered heteroaryl, optionally substituted with 1 or 2 substituents independently selected from $R^a$. For example, $R^2$ is selected form pyridinyl, pyrimidinyl, pyrazolyl, imidazolyl, and quinolinyl, each of which is optionally substituted with 1 or 2 independently selected $R^a$.

In some embodiments of Formula (II), $R^2$ is 4-10 membered heterocycloalkyl, optionally substituted with 1 or 2 substituents independently selected from $R^a$. For example, $R^2$ is selected from azetidinyl, pyrrolidinyl, piperidinyl, piperazinyl, oxazolidinyl and morpholinyl, each of which is optionally substituted with 1 or 2 substituents independently selected from $R^a$.

In some embodiments of Formula (II), $R^2$ is $C_{3-10}$ cycloalkyl, optionally substituted with 1 or 2 substituents independently selected from $R^a$. For example, $R^2$ is selected form cyclopropyl, cyclobutyl, cyclopentyl, cyclohexyl, and cyclopentyl, each of which is optionally substituted with 1 or 2 substituents independently selected from $R^a$.

In some embodiments of Formula (II), $R^2$ is selected from $C_{1-6}$ alkyl and $C_{6-10}$ aryl, each of which is optionally substituted with 1 or 2 substituents independently selected from $R^a$. In some embodiments of Formula (II), $R^2$ is selected from $C_{1-6}$ alkyl and $C_{6-10}$ aryl.

In some embodiments of Formula (II), $R^2$ is $C_{6-10}$ aryl, optionally substituted with 1 or 2 substituents independently selected from $R^a$. In some embodiments of Formula (II), $R^2$ is phenyl, optionally substituted with 1 or 2 substituents independently selected from $R^a$. In some embodiments of Formula (II), $R^2$ is phenyl.

In some embodiments of Formula (II), $R^2$ is $C_{1-6}$ alkyl. In some embodiments of Formula (II), $R^2$ is $C_{1-4}$ alkyl. In some embodiments of Formula (II), $R^2$ is $C_{1-6}$ alkyl optionally substituted with 1 or 2 substituents independently selected from $R^a$. In some embodiments of Formula (II), $R^2$ is methyl, ethyl, propyl, isopropyl, or tert-butyl. In some embodiments of Formula (II), $R^2$ is ethyl or tert-butyl. In some embodiments of Formula (II), $R^2$ is tert-butyl.

In some embodiments of Formula (II), $R^2$ is $C_{1-6}$ haloalkyl. In some embodiments of Formula (II), $R^2$ is $C_{1-4}$ haloalkyl. In some embodiments of Formula (II), $R^2$ is $C_{1-3}$ haloalkyl. In some embodiments of Formula (II), $R^2$ is trifluoromethyl, trichloromethyl, 2,2,2-trifluoroethyl, perfluoroethyl, or 1,1,1,3,3,3-hexafluoro-2-(trifluoromethyl)prop-2-yl.

In some embodiments of Formula (II), $R^2$ is selected from ethyl, tert-butyl, and phenyl.

In some embodiments of Formula (II), $R^a$ is selected from OH, $NO_2$, CN, halo, $C_{1-3}$ alkyl, $C_{1-3}$ haloalkyl, $C_{1-3}$ alkoxy, $C_{1-3}$ haloalkoxy, $NH_2$, $C_{1-3}$ alkylamino and di($C_{1-3}$ alkyl)amino.

In some embodiments of Formula (II), $R^a$ is selected from OH, $NO_2$, CN, halo, $C_{1-3}$ alkyl, $C_{1-3}$ haloalkyl, $C_{1-3}$ alkoxy and $C_{1-3}$ haloalkoxy.

In some embodiments of Formula (II), $R^a$ is selected from OH, $NO_2$, CN, halo, $C_{1-3}$ alkoxy and $C_{1-3}$ haloalkoxy.

In some embodiments of Formula (II), $R^a$ is selected from $NH_2$, $C_{1-3}$ alkylamino and di($C_{1-3}$ alkyl)amino.

In some embodiments of Formula (II), $R^a$ is $C_{1-3}$ alkyl.

In some embodiments of Formula (II), $R^a$ is selected from OH, $C_{1-3}$ alkoxy and $C_{1-3}$ haloalkoxy.

In some embodiments of Formula (II), $R^a$ is selected from $C_{1-3}$ alkyl, OH, $C_{1-3}$ alkoxy, $C_{1-3}$ haloalkoxy, $NH_2$, $C_{1-3}$ alkylamino and di($C_{1-3}$ alkyl)amino.

In some embodiments of Formula (II), $R^a$ is selected from $NO_2$, CN and halo.

In some embodiments of Formula (II):
$X^1$ is O;
L is $C_{1-3}$ alkylene;
ring A is a 4-6-membered heterocycloalkyl, optionally substituted with 1, 2, or 3 substituents independently selected from $R^a$;
W is O;
$X^2$ is O;

$R^2$ is selected from $C_{1-6}$ alkyl, $C_{1-6}$ haloalkyl, $C_{3-10}$ cycloalkyl and $C_{6-10}$ aryl, each of which is optionally substituted with 1, 2, or 3 substituents independently selected from $R^a$; and each $R^a$ is independently selected from OH, $NO_2$, CN, halo, $C_{1-3}$ alkoxy and $C_{1-3}$ haloalkoxy.

In some embodiments of Formula (II):
$X^1$ is O;
L is $C_{1-3}$ alkylene;
ring A is azetidinyl (e.g., azetidin-3-yl);
W is O;
$X^2$ is O; and
$R^2$ is $C_{1-6}$ alkyl.

In some embodiments, the compound of Formula (II) has Formula:

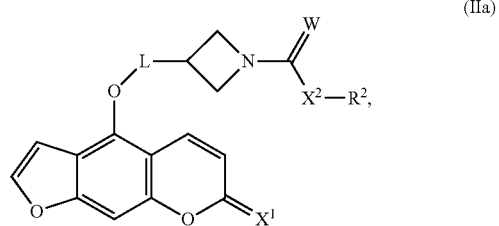

(IIa)

or a pharmaceutically acceptable salt thereof.

In some embodiments, the compound of Formula (II) has Formula:

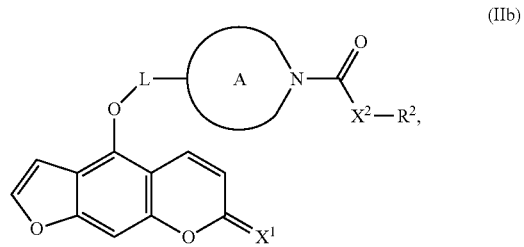

(IIb)

or a pharmaceutically acceptable salt thereof.

In some embodiments, the compound of Formula (II) has Formula:

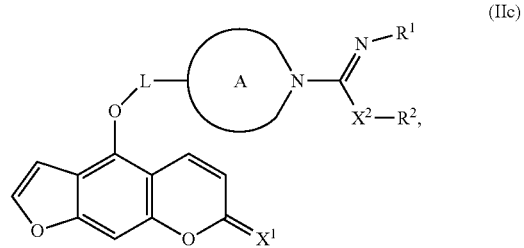

(IIc)

or a pharmaceutically acceptable salt thereof.

In some embodiments, the compound of Formula (II) has Formula:

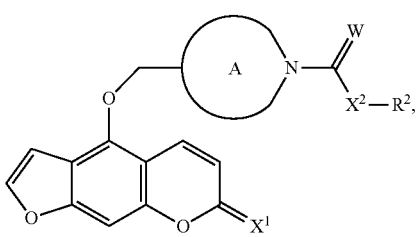

(IId)

or a pharmaceutically acceptable salt thereof.

In some embodiments, the compound of Formula (II) has formula:

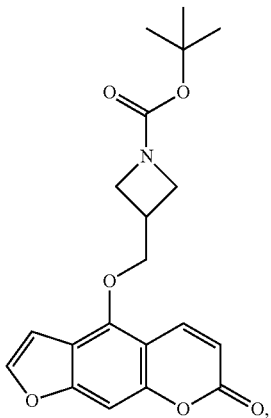 [SMILES: CC(C)(C)OC(=O)N1CC(COc2c3ccoc3cc3oc(=O)ccc23)C1]

or a pharmaceutically acceptable salt thereof.

The present application also provides, inter alia, a compound of Formula (III):

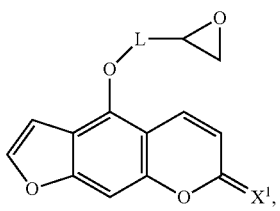

(III)

or a pharmaceutically acceptable salt thereof, wherein:
$X^1$ is selected from O and S; and
L is $C_{1-6}$ alkylene, optionally substituted with 1, 2, or 3 substituents independently selected from OH, $NO_2$, CN, halo, $C_{1-3}$ alkoxy, $C_{1-3}$ haloalkoxy, $NH_2$, $C_{1-3}$ alkylamino and di($C_{1-3}$ alkyl)amino.

In some embodiments of Formula (III), $X^1$ is O. In other embodiments of Formula (III), $X^1$ is S.

In some embodiments of Formula (III), L is a linear (straight chain) $C_{1-6}$ alkylene. In some embodiments of Formula (III), L is $C_{1-3}$ alkylene, optionally substituted with 1, 2, or 3 substituents independently selected from OH, $NO_2$, CN, halo, $C_{1-3}$ alkoxy, and $C_{1-3}$ haloalkoxy. In some embodiments of Formula (III), L is $C_{1-3}$ alkylene, optionally substituted with 1 or 2 substituents independently selected from $NO_2$, CN, halo, $C_{1-3}$ alkoxy, and $C_{1-3}$ haloalkoxy. In some embodiments of Formula (III), L is $C_{1-3}$ alkylene, optionally substituted with 1 or 2 substituents independently selected from $NO_2$, CN and halo. In some embodiments of Formula (III), L is $C_{1-3}$ alkylene, optionally substituted with 1 or 2 substituents independently selected from OH and $C_{1-3}$ alkoxy.

In some embodiments of Formula (III), L is selected from methylene and ethylene. In some embodiments of Formula (III), L is methylene.

In some embodiments, the compound of Formula (III) has Formula:

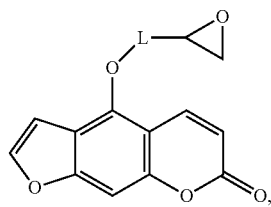

(IIIa)

or a pharmaceutically acceptable salt thereof.

In some embodiments, the compound of Formula (III) has formula:

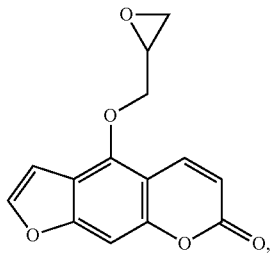 [SMILES: O=c1ccc2c(OCC3CO3)c3ccoc3cc2o1]

or a pharmaceutically acceptable salt thereof.

In some embodiments, a salt of a compound of Formulae I, II, or III is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formulae I, II, or III include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formulae I, II, or III include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formulae I, II, or III, or pharmaceutically acceptable salts thereof, are substantially isolated.

Methods of Making Therapeutic Compounds

Compounds of Formulae I, II, and III, including salts thereof, can be prepared using known organic synthesis techniques and can be synthesized according to any of numerous possible synthetic routes. For example, the compounds described herein may be prepared using methods and procedures similar to those of Examples 1-7 herein. A person skilled in the art knows how to select and implement appropriate synthetic protocols, and appreciates that the processes described are not the exclusive means by which compounds provided herein may be synthesized, and that a broad repertoire of synthetic organic reactions is available to be potentially employed in synthesizing compounds provided herein.

Suitable synthetic methods of starting materials, intermediates and products may be identified by reference to the literature, including reference sources such as: Advances in Heterocyclic Chemistry, Vols. 1-107 (Elsevier, 1963-2012); Journal of Heterocyclic Chemistry Vols. 1-49 (Journal of Heterocyclic Chemistry, 1964-2012); Carreira, et al. (Ed.) Science of Synthesis, Vols. 1-48 (2001-2010) and Knowledge Updates KU2010/1-4; 2011/1-4; 2012/1-2 (Thieme, 2001-2012); Katritzky, et al. (Ed.) Comprehensive Organic Functional Group Transformations, (Pergamon Press, 1996); Katritzky et al. (Ed.); Comprehensive Organic Functional Group Transformations II (Elsevier, 2$^{nd}$ Edition, 2004); Katritzky et al. (Ed.), Comprehensive Heterocyclic Chemistry (Pergamon Press, 1984); Katritzky et al., Comprehensive Heterocyclic Chemistry II, (Pergamon Press, 1996); Smith et al., March's Advanced Organic Chemistry: Reactions, Mechanisms, and Structure, 6$^{th}$ Ed. (Wiley, 2007); Trost et al. (Ed.), Comprehensive Organic Synthesis (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, Protective Groups in Organic Synthesis, 4$^{th}$ Ed., Wiley & Sons, Inc., New York (2006).

Methods of Using Therapeutic Compounds

In some embodiments, the compounds of any one of Formulae (I)-(III) inhibit induction of a Cytochrome P450 family 1 (CYP1) enzyme in a cardiomyocyte. In other embodiments, the compounds of any one of Formulae (I)-(III) directly inhibit activity of a Cytochrome P450 family 1 (CYP1) enzyme in a cardiomyocyte. CYP1 is a family of highly conserved monooxygenases responsible for the metabolism of environmental toxicants including polycyclic aromatic hydrocarbons (Shimada and Fujii-Kuriyama, 2004). In addition, CYP1 enzymes play an important role in the metabolism of endogenous bioactive polyunsaturated fatty acids (Divanovic et al., 2013) such as the hydroxyeicosatetraenoic acids (HETEs), arachidonic acid metabolites which have been previously implicated in the pathogenesis of other cardiovascular diseases such as hypertension (Jenkins et al., 2009). Human and mouse CYP1 enzymes are divided into two subfamilies: 1A1/1A2 and 1B1. Zebrafish CYP1 enzymes are divided into four subfamilies, two of which are homologous to those found in mammalian species: 1A, 1B1,1C1/1C$_2$ (may complement 1B1 activity in fish), and 1D1 (pseudogene in humans) (Goldstone et al., 2010). In some embodiments, the compounds of any one of Formulae (I)-(III) affect activity (e.g., inhibit induction and/or directly inhibit activity) of CYP1A and/or CYP1B1. In some embodiments, the expression of Cytochrome P450 family 1 (CYP1) enzyme in a cardiomyocyte is induced by contacting the cardiomyocyte with an anthracycline chemotherapeutic agent.

In some embodiments, the anthracycline chemotherapeutic agent is an antineoplastic antibiotic having an anthracenedione (i.e., anthraquinone or dioxoanthracene) structural core:

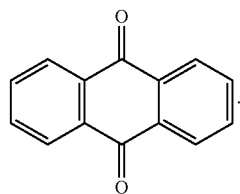 [SMILES: O=C1c2ccccc2C(=O)c2ccccc21]

Suitable examples of anthracycline chemotherapeutic agents include daunorubicin, doxorubicin, epirubicin, idarubicin, valrubicin, ditrisarubicins, and mitoxantrone. In some embodiments, the anthracycline chemotherapeutic agent is doxorubicin (DOX, CAS Registry No. 23214-92-8) having the following structural formula:

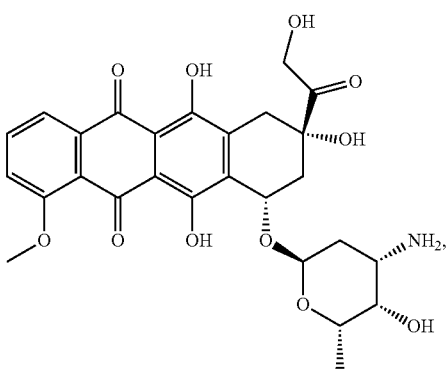 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

or a pharmaceutically acceptable salt thereof (e.g., DOX hydrochloride).

In some embodiments, the compounds of any one of Formulae (I)-(III) modulate aryl hydrocarbon receptor (AHR) in a cardiomyocyte. AHR is a transcriptional regulator, which translocates to the nucleus to induce expression of the CYP1 family of enzymes (Volkova et al., 2011). In accordance with the Examples provided herein, DHRS13L1, THBS1B, and GSTP2 were induced in zebrafish treated with DOX. Expression levels of these genes have been previously reported to correlate with AHR activity (Dabir et al., 2008; Goodale et al., 2015; Van Tiem and Di Giulio, 2011). In some embodiments, the compounds of any one of Formulae (I)-(III) are antagonists of aryl hydrocarbon receptor (AHR) in a cardiomyocyte. In some embodiments, the compounds of any one of Formulae (I)-(III) inhibit AHR-mediated transcription of CYP1 family genes. In some embodiments, the activity of AHR in a cardiomyocyte is enhanced by contacting the myocyte with an anthracycline chemotherapeutic agent such as DOX. In some embodiments, the aryl hydrocarbon receptor (AHR) is activated by contacting the cardiomyocyte with an anthracycline chemotherapeutic agent such as DOX. In some embodiments, the enhanced activity of AHR and/or CYP1 family enzymes induces apoptosis in a cardiomyocyte.

In one general aspect, the present application provides a method of inhibiting induction of a Cytochrome P450 family 1 (CYP1) enzyme in a cardiomyocyte, the method comprising contacting the cardiomyocyte with a compound of any one of Formulae (I)-(III), or a pharmaceutically acceptable salt thereof.

In another general aspect, the present application provides a method of inhibiting a Cytochrome P450 family 1 (CYP1) enzyme in a cardiomyocyte, the method comprising contacting the cardiomyocyte with a compound of any one of Formulae (I)-(III), or a pharmaceutically acceptable salt thereof.

In yet another general aspect, the present application provides a method of modulating an aryl hydrocarbon receptor (AHR) in a cardiomyocyte, the method comprising contacting the cardiomyocyte with a compound of any one of Formulae (I)-(III), or a pharmaceutically acceptable salt thereof.

In yet another general aspect, the present application provides a method of inhibiting apoptosis in a cardiomyocyte, the method comprising contacting the cardiomyocyte with a compound of any one of Formulae (I)-(III), or a pharmaceutically acceptable salt thereof. In some embodiments, the apoptosis in the cardiomyocyte is associated with elevated levels of CYP1 enzymes and/or AHR, and concomitantly the elevated levels of reactive oxygen species (ROS) and oxidative stress, in the cardiomyocyte. In some embodiments, the elevated levels of CYP1 enzymes and/or AHR in the cardiomyocyte are induced by an anthracycline chemotherapeutic agent (e.g., DOX). In some embodiments, the apoptosis in the cardiomyocyte is induced by an anthracycline chemotherapeutic agent such as DOX.

In some embodiments, the cardiomyocyte is contacted in vitro, in vivo, or ex vivo.

In yet another general aspect, the present application provides a method of treating or preventing cardiotoxicity (or cardiomyopathy) in a subject, the method comprising administering to the subject (e.g., subject in need of such treatment or prevention) a therapeutically effective amount of a compound of any one of Formulae (I)-(III), or a pharmaceutically acceptable salt thereof. In some embodiments, the cardiotoxicity (or cardiomyopathy) in the subject is induced by administration to the subject an amount of an anthracycline chemotherapeutic agent that is sufficient to induce apoptosis in a cancer cell. In some embodiments, administration of the compound of any one of Formulae (I)-(III), or a pharmaceutically acceptable salt thereof, to the subject does not substantially inhibit anthracycline-induced apoptosis in a cancer cell. For example, administration to the subject of an amount of a compound of any one of Formulae (I)-(III), or a pharmaceutically acceptable salt thereof, that is therapeutically effective to treat or prevent cardiotoxicity (or cardiomyopathy) in the subject does not interfere with ability of the anthracycline chemotherapeutic agent to kill a tumor cell.

In some embodiments, the cardiotoxicity (or cardiomyopathy) is grade 2 toxicity or higher according to NCI nomenclature. For example, cardiotoxicity is moderate (grade 2), severe (grade 3), or life-threatening (grade 4). In some embodiments, the cardiotoxicity is characterized by cardiotoxic events such as pericardial edema, impaired cardiac contractility, decreased blood flow through the vasculature, left ventricular ejection fraction (LVEF) of less than 55% (e.g., less than 50%), congestive heart failure (e.g., irreversible CHF), abnormal heartbeat, impaired myocardial function, fractional shortening in cardiomyocytes, reduction of strain rate in cardiomyocytes. Cardiotoxicity can also be diagnosed based on abnormal markers of cardiac injury (e.g., troponin) or a decline in strain/strain rate on echocardiography. Suitable examples of cardiomyopathies include hypertrophic cardiomyopathy, dilated cardiomyopathy, restrictive cardiomyopathy, arrhythmogenic right ventricular dysplasia, and broken heart syndrome. In hypertrophic cardiomyopathy, the heart muscle enlarges and thickens. In dilated cardiomyopathy, the ventricles enlarge and weaken. In restrictive cardiomyopathy, the ventricle stiffens. In some embodiments, the method of treating cardiotoxicity (or cardiomyopathy) in the subject includes ameliorating symptoms of cardiotoxicity such as shortness of breath, feeling tired, swelling of the legs, heart failure, abnormal heartbeat, chest discomfort, fainting and fatigue.

In some embodiments of any of the foregoing methods, an anthracycline chemotherapeutic agent (e.g., DOX) is administered to the subject at a maximum safe dosage tolerated in cancer treatment. The maximum safe dosage may be approximately 400-500 mg/m$^2$ or any suitable dosage greater than 400 mg/m$^2$, based on factors related to each individual patient's disease state.

In yet another general aspect, the present application provides a method of preventing cardiotoxicity in a subject receiving cardiotoxic chemotherapy, comprising administering to the subject (e.g., in need thereof) a therapeutically effective amount of a compound of any one of Formulae (I)-(III), or a pharmaceutically acceptable salt thereof. In one example, the cardiotoxic chemotherapy includes administering to the subject a therapeutically effective amount of anthracycline chemotherapeutic agent (e.g., DOX). In some embodiments, the compound of any one of Formulae (I)-(III), or a pharmaceutically acceptable salt thereof, is administered to the subject prior to cardiotoxic chemotherapy. For example, the compound of any one of Formulae (I)-(III), or a pharmaceutically acceptable salt thereof, may be administered to the subject at least 5 min, at least 15 min, at least 30 min, at least 24 hours or at least 3 days, or at least 1 week prior to cardiotoxic chemotherapy. In certain embodiments, the compound of any one of Formulae (I)-(III), or a pharmaceutically acceptable salt thereof, may be administered to the subject at least 5 min, at least 15 min, at least 30 min, or at least 60 min after administration of cardiotoxic chemotherapy. In yet other embodiments, the compound of any one of Formulae (I)-(III), or a pharmaceutically acceptable salt thereof, may be administered to the subject simultaneously with cardiotoxic chemotherapy, for example, in a single dosage form with a cardiotoxic chemotherapeutic agent (e.g., doxorubicin).

In yet another general aspect, the present application provides a method of enhancing antitumor effect of an anthracycline chemotherapeutic agent (such as DOX), comprising administering to the subject (e.g., in need thereof) a therapeutically effective amount of a compound of any one of Formulae (I) or a pharmaceutically acceptable salt thereof. In one example, the compound of any one of Formulae (I)-(III) enhances the antitumor effect of doxorubicin by counteracting doxorubicin-induced expression of the Cytochrome P450 family 1 (CYP1) enzymes in cardiac muscle cells, thereby providing cardioprotection to the subject. In this example, the subject's chance of survival may be increased by using a higher dose of doxorubicin to treat cancer in the subject, with the reduced risk of cardiotoxic adverse events associated with doxorubicin therapy.

In some embodiments, the compound of any one of Formulae (I)-(III), or a pharmaceutically acceptable salt thereof, may be administered to the subject in combination with another cardioprotective therapeutic agent. Suitable examples of cardioprotective agents include cardioprotective drugs (e.g., dexrazoxane, ACE-inhibitors, diuretics, cardiac glycosides), cholesterol lowering drugs, revascularization drugs, anti-inflammatory drugs, cardioprotective diets, cardioprotective nutrients, cardioprotective herbs, cardioprotective vitamins (e.g., folic acid, B vitamin family), beta-blockers (e.g., acebutolol, atenolol, bisoprolol, metoprolol, nadolol, nebivolol, or propranolol), angiotensin receptor blockers (also called ARBs or angiotensin II inhibitors) (e.g., azilsartan, candesartan, eprosartan, irbesartan, losartan, olmesartan, telmisartan, or valsartan), and cardioprotective hormone treatments. In some embodiments, a therapeutically effective amount of the compound of any one of Formulae (I)-(III), or a pharmaceutically acceptable salt thereof, may be administered to the subject in combination with a therapeutically effective amount of dexrazoxane, or a pharmaceutically acceptable salt thereof.

In yet another general aspect, the present application provides a method of treating cancer in a subject, comprising administering to the subject (e.g., subject in need of cancer treatment) a therapeutically effective amount of a compound of any one of Formulae (I)-(III), or a pharmaceutically acceptable salt thereof, and an anthracycline chemotherapeutic agent, or a pharmaceutically acceptable salt thereof.

In some embodiments, cancer is selected from the group selected from sarcoma, angiosarcoma, fibrosarcoma, rhabdomyosarcoma, liposarcoma, myxoma, rhabdomyoma, fibroma, lipoma, teratoma, lung cancer, breast cancer, bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney, adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CIVIL), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, adrenal gland cancer, and neuroblastoma.

In the method of treating cancer, the compound of any one of Formulae (I)-(III) and the anthracycline chemotherapeutic agent may be administered to the subject simultaneously (e.g., in the same dosage form or in separate dosage forms), or consecutively (e.g., anthracycline chemotherapeutic agent may be administered before or after the compound of any one of Formulae (I)-(III)).

In some embodiments, the subject of the combination cancer treatment as described herein does not develop a cardiotoxicity or a cardiomyopathy associated with the administration of the anthracycline chemotherapeutic agent. In such embodiments, the cardiotoxicity or the cardiomyopathy may be characterized by any one of cardiotoxic events of symptoms described herein.

In some embodiments, the method of treating cancer in a subject comprises administering to the subject a total cumulative dose of about 200 mg/m$^2$ to about 500 mg/m$^2$ of doxorubicin, or a pharmaceutically acceptable salt thereof, and from about 0.1 mg/kg to about 2 mg/kg of the compound of any one of Formulae (I)-(III), or a pharmaceutically acceptable salt thereof. In some aspects of these embodiments, the total cumulative dose of doxorubicin is from about 220 mg/m$^2$ to about 500 mg/m$^2$, about 240 mg/m$^2$ to about 500 mg/m$^2$, or about 240 mg/m$^2$ to about 300 mg/m$^2$. In some embodiments, e.g., when the cancer is breast cancer, the total anthracycline dose may be about 240 mg/m$^2$ or less. In some embodiments, the total anthracycline dose if less than about 200 mg/m$^2$. In other embodiments, the total anthracycline dose is greater than about 500 mg/m$^2$.

In some embodiments, the method of treating cancer in a subject comprises administering to the subject a total cumulative dose of about 300 mg/m$^2$ to about 500 mg/m$^2$ of doxorubicin, or a pharmaceutically acceptable salt thereof, and from about 0.1 mg/kg to about 2 mg/kg of the compound of any one of Formulae (I)-(III), or a pharmaceutically acceptable salt thereof. In some aspects of these embodiments, the compound of any one of Formulae (I)-(III), or a pharmaceutically acceptable salt thereof, is administered once daily, twice daily, thrice daily, every other day, every two days, every three days, once weekly, twice weekly, once every two weeks, or once a month, and the doxorubicin, or a pharmaceutically acceptable salt thereof, is administered according to the regimen described in the FDA-approved drug label (Pfizer NDA050629). In other aspects of these embodiments, doxorubicin, or a pharmaceutically acceptable salt thereof, is administered to the subject by parenteral injection (e.g., infusion), and the compound of any one of Formulae (I)-(III), or a pharmaceutically acceptable salt thereof, is administered to the subject orally. In yet other aspects of these embodiments, doxorubicin, or a pharmaceutically acceptable salt thereof, and the compound of any one of Formulae (I)-(III), or a pharmaceutically acceptable salt thereof, are both administered by parenteral injection (e.g., infusion).

In some embodiments, the method of treating cancer in a subject further comprises administering to the subject an additional therapeutic agent, or pharmaceutically acceptable salt thereof. Suitable examples of additional therapeutic agents include an anti-HER2 agent (e.g., trastuzumab, pertuzumab, lapatinib), a pain relief agent (e.g., a nonsteroidal anti-inflammatory drug such as celecoxib or rofecoxib), an antinausea agent, or an additional anticancer agent (e.g., paclitaxel, docetaxel, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, taxol, herceptin, avastin, cytarabine, dactinomycin, interferon alpha, streptozocin, prednisolone, irinotecan, sulindac, 5-fluorouracil, capecitabine, oxaliplatin/5 FU, abiraterone, letrozole, 5-aza/romidepsin, or procarbazine). In certain embodiments, the anticancer agent is paclitaxel or docetaxel. In other embodiments, the anticancer agent is cisplatin or irinotecan. In some embodiments, the method of treating cancer in a subject further comprises administering to the subject a cell carcinoma treatment. Examples of additional optional renal cell carcinoma treatments include, without limitation, treatment with Nexavar®, Sutent®, Torisel®, Afinitor® (everolimus), axitinib, pazopanib, levatinib, interleukin-2, and combinations thereof. In some embodiments, the method of treating cancer in a subject further comprises administering to the subject a proteasome inhibitor. Exemplary proteasome inhibitors include lactacystin, bortezomib, dislfiram, salinosporamide A, carfilzomib, ONX0912, CEP-18770, MLN9708, epoxomicin, and MG132). Non-limiting examples of proteasome inhibitors include marizomib (NPI-0052), bortezomib (Velcade®), and carfilzomib (Kyprolis®).

In some embodiments, the method of treating cancer in a subject also comprises administering to the subject a therapeutically effective amount of an additional cardioprotective therapeutic agent. Suitable examples of such agents are described herein.

Pharmaceutical Compositions and Formulations

The present application also provides pharmaceutical compositions comprising an effective amount of a compound of any one of Formulae (I)-(III) disclosed herein, or a pharmaceutically acceptable salt thereof; and a pharmaceutically acceptable carrier. The pharmaceutical composition may also comprise any one of the additional therapeutic agents described herein (e.g., doxorubicin or an additional cardioprotective agent). In certain embodiments, the application also provides pharmaceutical compositions and dosage forms comprising any one the additional therapeutic agents described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain any one of the compounds and therapeutic agents described herein in the range of 0.005% to 100% with the balance made up from the suitable pharmaceutically acceptable excipients. The contemplated compositions may contain 0.001%400% of any one of the compounds and therapeutic agents provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration may be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol,* 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds and therapeutic agents of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a therapeutic agent, or a composition comprising a compound of the present application or a therapeutic agent, such that said compound or therapeutic agent is released from said device and is therapeutically active.

Dosages and Regimens

In the pharmaceutical compositions of the present application, a compound of any one of Formulae (I)-(III) is present in an effective amount (e.g., a therapeutically effective amount).

Effective doses may vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, an effective amount of a compound of any one of Formulae (I)-(III) can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of a compound of any one of Formulae (I)-(III) is about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month).

Kits

The present invention also includes pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit. The kit may optionally include an anthracycline such as doxorubicin, in any one of amounts and dosage forms described herein.

EXAMPLES

Materials and Methods

Compounds and Reagents 4-hydroxypsoralen (bergaptol or 4-hydroxy-7H-furo[3,2-g]chromen-7-one, CAS Registry No. 486-60-2) was prepared according to the methods and procedures similar to those described in Liu et al. (2014) Visnagin protects against doxorubicin-induced cardiomyopathy through modulation of mitochondrial malate dehydrogenase, Science translational medicine 6, 266ra170. Commercially available compounds were purchased from Sigma-Aldrich unless otherwise specified.

Animals

All zebrafish and mouse experiments were reviewed and approved by the Massachusetts General Hospital (MGH) Institutional Animal Care and Use Committee.

Zebrafish Doxorubicin Model

Zebrafish embryos at 30 hours post-fertilization were treated with DOX at 100 µM in 96-well plates as previously described (Liu et al., 2014). Tested compounds were dissolved in DMSO and added at concentrations ranging from 3 nM to 10 µM (n=6 fish per dose; <1% DMSO v/v). The cardiomyopathy phenotype (decreased cardiac contraction, pericardial edema, and decreased tail blood flow) was assessed under light microscopy (5× magnification) at 40 hours post-treatment (hpt). Percent rescue from the cardiomyopathy phenotype was calculated for each concentration tested. Zebrafish were considered to be rescued from DOX-induced cardiomyopathy if all three features of the phenotype were absent. For the tested compounds, each dose-response experiment was repeated three times.

Dose-response curves were constructed using Prism (GraphPad). Raw data representing percent rescue at each dose was log-transformed, and $EC_{50}$ values were calculated using nonlinear regression analysis. The median toxic dose ($TD_{50}$) was defined for each compound by assessing for pericardial edema, non-specific deformities, and death in the absence of doxorubicin treatment (data not shown). Concentrations at and above the $TD_{50}$ (toxic dose) were excluded from dose-response curves.

Fluorescence Reflectance Imaging

DOX fluorescence imaging was carried out on IVIS spectrum with the filter setting 500 nm excitation/600 nm emission, 30 second exposure, with 135 µm in-plane resolution. A series of DOX phantoms, ranging from 0 to 0.03 mM was prepared in saline, and imaged on the IVIS spectrum with identical settings. Anx-750 fluorescence was detected with the filter setting 745 nm excitation/800 nm emission, 30 second exposure, and 135 μm resolution.

Image Quantification and Analysis

Annexin and DOX fluorescence signal was quantified and analyzed in ImageJ (National Institute of Health). For each heart, fluorescence intensity was averaged across 4-6 slices. Annexin uptake was normalized to the saline injected control animals. DOX fluorescence in the heart was quantified by calculating the signal-to-noise ratio (SNR=mean fluorescence intensity$_{heart}$/standard deviation$_{air}$). A threshold of two standard deviations above the saline injected control animals was applied to all DOX injected animals, with or without therapeutics. Only animals that met the threshold (thus DOX positive hearts) were included in the analysis. All statistical analysis was performed in Prism (Graphpad).

Cultured HL-1 Cardiomyocyte Model

The cardiomyocyte cell line HL-1 derived from mouse atrial tumor was a gift from W. Claycomb. Cells were cultured as previously published (Claycomb et al., 1998) and treated with doxorubicin 5 μM with or without the tested compounds at a concentration up to 50 μM. Viability was assessed after 18 hours of using a CellTiter-Glo Luminescent assay from Promega. Each dose-response experiment was repeated three times.

Zebrafish Proteomics

Zebrafish embryos were treated with DMSO, DOX, DOX+visnagin 20 μM, or visnagin 20 μM as described. 105 embryos were treated per condition and lysed in ultrapure water at 40 hours post-treatment. Proteomics analyses were performed by OmicScouts in collaboration with Merck. Following protein digestion, peptides from each treatment condition were labeled using isobaric tandem mass tags (TMT[10]-plex) followed by fractionation and analysis by liquid chromatography-tandem mass spectrometry (LC-MS/MS). 55,444 peptide sequences were identified and 6,085 proteins were quantified.

Zebrafish CYP1 Experiments

For RT-qPCR, zebrafish embryos were treated as described and lysed in RNAzol RT at 40 hpt for isolation of RNA. cDNA was synthesized using the QuantiTect Reverse Transcription Kit from Qiagen. PCR primers for zebrafish cyp1a and cyp1b1 were used as previously published (Jonsson et al., 2007). For Western blotting, zebrafish were treated as described and homogenized in lysis buffer (10 mM Tris [pH 7.4]; 150 mM NaCl; 1 mM CaCl$_2$); 1% Triton X-100; supplemented with protease inhibitor cocktail and phosphatase inhibitor) at 40 hpt using a motorized pestle. The homogenate was centrifuged for 10 minutes at 14,000 g at 4° C. and protein concentration of the supernatant was assessed using a Pierce BCA Protein Assay Kit from ThermoFisher Scientific. Following SDS-PAGE, proteins were transferred to a polyvinylidene difluoride membrane (Bio-Rad), blocked with 5% dry milk, and incubated with zebrafish-specific anti-CYP1A1 antibody (Abcam) at 4° C. overnight. Immunodetection was performed using a mouse anti-rabbit IgG light-chain specific secondary antibody (Jackson ImmunoResearch) and Amersham ECL Prime Western Blotting Detection Reagent (GE Healthcare Life Sciences).

CYP Inhibition Assays

CYP inhibition experiments were performed by Cerep Panlabs (Eurofins) using human liver microsomes and the following substrates: phenacetin 10 μM (CYP1A), buproprion 100 μM (CYP2B6), paclitaxel 10 μM (CYP2C8), diclofenac 10 μM (CYP 2C9), omeprazole 0.5 μM (CYP2C19), dextromethorphan 5 μM (CYP2D6), and testosterone 50 μM (CYP3A). Metabolites of each substrate were measured using LC-MS/MS. Mean percent inhibition was calculated using the following reference inhibitors: furafylline (CYP1A), clopidogrel (CYP2B6), montelukast (CYP2C8), sulfaphenazole (CYP2C9), oxybutynin (CYP2C19), quinidine (CYP2D6), and ketoconazole (CYP3A). For compounds demonstrating mean inhibition greater than 50%, a full dose-response experiment was performed to calculate the half-maximal inhibitory concentration (IC$_{50}$). All concentrations were tested in duplicate to obtain the final results.

Example 1—Preparation of 4-(oxiran-2-ylmethoxy)-7H-furo[3,2-g]chromen-7-one

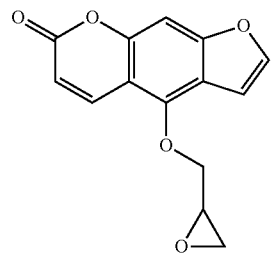 [SMILES: O=c1ccc2c(OCC3CO3)c3ccoc3cc2o1]

Under a N$_2$ atmosphere, 4-hydroxypsoralen (45 mg, 0.225 mmol) was dissolved in anhydrous DMF (1 mL/mmol), and treated with K$_2$CO$_3$ (47 mg, 0.3375 mmol) and KI (cat.). Epibromohydrin (CAS Registry No. 3132-64-7; 0.225 mmol) was added and the reaction was stirred at 50° C. for 8 h. The reaction mixture was diluted with EtOAc and poured onto 1N HCl. The aqueous phase was then extracted three times with EtOAc. The combined organic layers were washed with H$_2$O and brine, dried with MgSO$_4$, and concentrated. The residue was purified via column chromatography eluting with EtOAc/Hexanes to obtain the product.

Example 2—Preparation of tert-butyl (3-((7-oxo-7H-furo[3,2-g]chromen-4-yl)oxy)propyl)carbamate

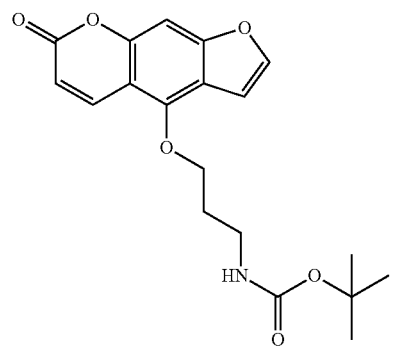 [SMILES: CC(C)(C)OC(=O)NCCCOc1c2ccoc2cc2oc(=O)ccc12]

4-Hydroxypsoralen (40 mg, 0.2 mmol), 3-(Boc-amino) propyl bromide (CAS Registry No. 83948-53-2; 48 mg, 0.2 mmol), and potassium carbonate (42 mg, 0.3 mmol) were mixed in dimethylformamide (DMF) (1 mL). The reaction mixture was heated under reflux until TLC analysis (EA: Hex=1:1, Rf=0.4) confirmed that the reaction was complete. Water was added and the mixture was extracted with ethyl acetate. The combined organic extracts were washed with brine, dried over Na$_2$SO$_4$, and the solvent was removed in vacuo. The residue was purified via column chromatography, yield 90% (65 mg, 0.18 mmol). $^1$H NMR (500 MHz, CDCl$_3$) δ 8.16 (d, J=9.5 Hz, 1H), 7.59 (d, J=4.5 Hz, 1H), 7.26 (d, J=6.5 Hz, 1H,), 7.15 (d, J=6.5 Hz, 1H), 6.99 (s, 1H), 6.29 (d, J=9.5 Hz, 1H), 4.52 (t, J=6.0 Hz, 2H), 3.41 (t, J=5.0 Hz, 2H,), 2.12-2.05 (m, 2H), 1.46 (s, 9H); ESI-MS m/z 359.7 (M+).

Example 3—Preparation of tert-butyl (2-07-oxo-7H-furo[3,2-g]chromen-4-yl)oxy)ethyl)carbamate

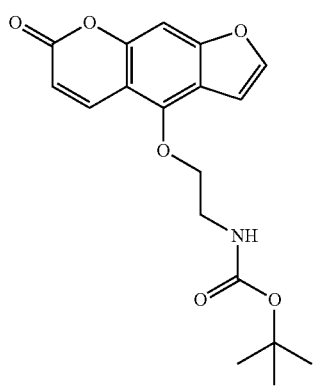 [SMILES: CC(C)(C)OC(=O)NCCOc1c2ccoc2cc2oc(=O)ccc12]

The title compound was prepared using methods and procedures similar to those described in Example 2, using tert-butyl (2-bromoethyl)carbamate (CAS Registry No. 39684-80-5) instead of 3-(Boc-amino)propyl bromide.

Example 4—Preparation of tert-butyl 3-(((7-oxo-7H-furo[3,2-g]chromen-4-yl)oxy)methyl)azetidine-1-carboxylate

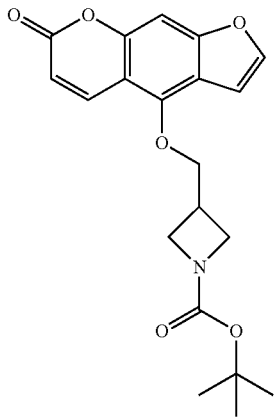 [SMILES: CC(C)(C)OC(=O)N1CC(COc2c3ccoc3cc3oc(=O)ccc23)C1]

The title compound was prepared using methods and procedures similar to those described in Example 1, using tert-butyl 3-(bromomethyl)azetidine-1-carboxylate (CAS Registry No. 253176-93-1) instead of epibromohydrin.

Example 5—S-ethyl (2-((7-oxo-7H-furo[3,2-g]chromen-4-yl)oxy)ethyl)carbamothioate

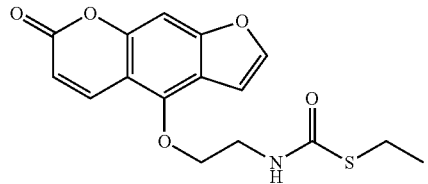 [SMILES: CCSC(=O)NCCOc1c2ccoc2cc2oc(=O)ccc12]

Step 1—Preparation of 4-(2-aminoethoxy)-7H-furo[3,2-g]chromen-7-one

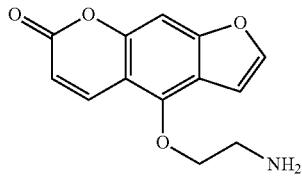 [SMILES: NCCOc1c2ccoc2cc2oc(=O)ccc12]

TFA (4 mL) was added to a stirred solution of the compound of Example 3 in DCM (4 mL). The mixture was allowed to stir for 5 h, after which time the reaction was diluted EtOAc. The aqueous phase was extracted three times with EtOAc (3×10 mL) and the combined organic layers were washed with NaHCO$_3$ (15 mL), brine (15 mL), H$_2$O (15 mL), dried with MgSO$_4$ and concentrated. The residue was purified via column chromatography eluting with EtOAc/Hexanes to obtain the title compound of Step 1. $^1$H NMR (500 MHz, Methanol-d$_4$) δ 8.38 (s, 1H), 7.79 (d, J=2.5 Hz, 1H), 7.17 (d, J=17.2 Hz, 2H), 6.27 (dd, J=9.9, 2.3 Hz, 1H), 4.73 (d, J=6.2 Hz, 2H), 3.53 (d, J=7.3 Hz, 2H).

Step 2—Preparation of S-ethyl (2-((7-oxo-7H-furo[3,2-g]chromen-4-yl)oxy)ethyl)carbamothioate Under a N$_2$ atmosphere, the compound obtained in step 1 was dissolved in anhydrous DCM (1 mL/mmol), and treated with triethylamine (10 eq). The S-ethyl chloridothiocarbonate (CAS Registry No. 2941-64-2; 10 eq) was added and the reaction stirred at 0° C. for 4-8 h. After this time the reaction was diluted with EtOAc and poured onto 1N HCl. The aqueous phase was then extracted three times with EtOAc. The combined organic layers were washed with brine, H$_2$O, dried with MgSO$_4$ and concentrated. The residue was purified via column chromatography eluting with EtOAc/Hexanes to obtain the title product. $^1$H NMR (500 MHz, Chloroform-d) δ 8.08 (d, J=9.8 Hz, 1H), 7.56 (d, J=2.3 Hz, 1H), 7.02 (s, 1H), 6.90 (d, J=2.4 Hz, 1H), 6.21 (d, J=9.8 Hz, 2H), 4.49 (t, J=5.2 Hz, 2H), 3.78 (d, J=5.5 Hz, 2H), 2.93 (q, J=7.4 Hz, 2H), 1.29 (t, J=7.4 Hz, 3H).

Example 6—phenyl (3-07-oxo-7H-furo[3,2-g]chromen-4-yl)oxy)propyl)carbamate

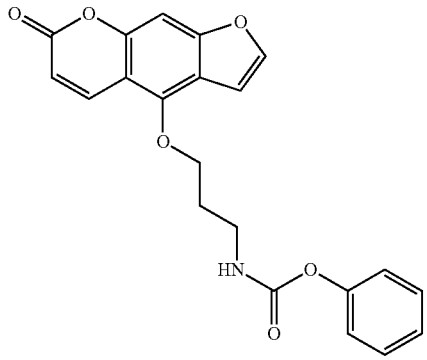 [SMILES: O=C(NCCCOc1c2ccoc2cc2oc(=O)ccc12)Oc1ccccc1]

The title compound was prepared using methods and procedures similar to those described in Example 1, using phenyl (3-bromopropyl)carbamate (available commercially) instead of epibromohydrin.

Example 7—Preparation of tert-butyl (2-((7-thioxo-7H-furo[3,2-g]chromen-4-yl)oxy)ethyl)carbamate

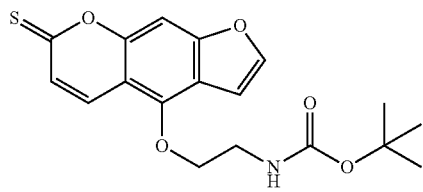 [SMILES: CC(C)(C)OC(=O)NCCOc1c2ccoc2cc2oc(=S)ccc12]

Under a N2 atmosphere, 4-hydroxy-7-thionepsoralen (prepared from the psoralen) was dissolved in anhydrous DMF (1 mL/mmol), and treated with $K_2CO_3$ (2 eq) and KI (cat.). The 2-(Boc-amino)ethyl bromide (1.2 eq) was added and the reaction stirred at 50° C. for 8 h. The reaction mixture was diluted with EtOAc and poured onto 1N HCl. The aqueous phase was then extracted three times with EtOAc. The combined organic layers were washed with $H_2O$, brine, dried with $MgSO_4$ and concentrated. The residue was purified via column chromatography eluting with EtOAc/Hexanes to obtain the title compound. 50% yield, $^1$H NMR (500 MHz, Chloroform-d) δ 7.91 (d, J=9.3 Hz, 1H), 7.64 (d, J=2.4 Hz, 1H), 7.32 (s, 1H), 7.12 (d, J=9.5 Hz, 1H), 6.99-6.95 (m, 1H), 4.93 (s, 1H), 4.51 (t, J=4.8 Hz, 2H), 3.64 (t, J=4.6 Hz, 2H), 1.46 (s, 9H).

Example 8—Compound of Example 2 Attenuates DOX-Induced Cardiac Apoptosis in Mice The compound of Example 2 having $EC_{50}$ of 7 nM and toxic dose of $TD_{50}$>10 µM in the zebrafish model was tested in a mouse model of acute DOX-induced cardiotoxicity.

Mouse Annexin Model

Doxorubicin was dissolved in 0.9% normal saline and administered at a dose of 15 mg/kg to adult $C_{57}$/B16 mice via i.p. injection. For the treatment arm, compound of example 2 was dissolved in 10% DMSO and 90% olive oil (carrier) or carrier alone was administered via intraperitoneal injection on the contralateral side.

A total of 45 mice were included in the study. Mice cohorts imaged were:
A) 0.9% saline, i.p. injection (n=7)
B) 15 mg/kg Doxorubicin in saline, and carrier only, i.p. (n=17)
C) 15 mg/kg Doxorubicin in saline, and 0.1 mg/kg example 2, i.p. (n=7)
D) 15 mg/kg Doxorubicin in saline, and 1 mg/kg example 2, i.p. (n=7)
E) 15 mg/kg Doxorubicin in saline, and 2 mg/kg example 2, i.p. (n=7)

Twenty-two hours after DOX and treatment injections, Anx-750 (Annexin Vivo 750, Perkin Elmer) was injected intravenously according to manufacturer's instructions. After 2 hours of probe circulation, hearts were excised, sectioned into 1-mm slices along the short axis, and imaged on a commercial imaging system (IVIS spectrum, Perkin Elmer) to assess apoptosis as previously described (Chen et al., 2011).

DOX uptake in the heart was assessed by reflectance fluorescence imaging, and the resultant apoptosis was simultaneously imaged with Anx-750, a near-infrared fluorescent Annexin V probe (Annexin-Vivo 750 is an Annexin V conjugate with a near-infrared fluorochrome, see Chen et al., 2011). Results of this experiment are shown in FIGS. 1A-1D. A significant reduction in apoptosis was seen with all three doses of Example 2 tested. Referring to FIGS. 1A-1D, * p<0.05,  p<0.01, and * p<0.001, ANOVA. Carrier=10% DMSO+90% olive oil.

Annexin uptake was reduced significantly with treatment with the Example 2 compound. Example 2 administered at doses of 0.1 mg/kg, 1 mg/kg, and 2 mg/kg conferred a significant cardioprotective effect. Positive DOX uptake in the heart was confirmed by direct imaging (fluorescence reflectance imaging).

Figure 1B:
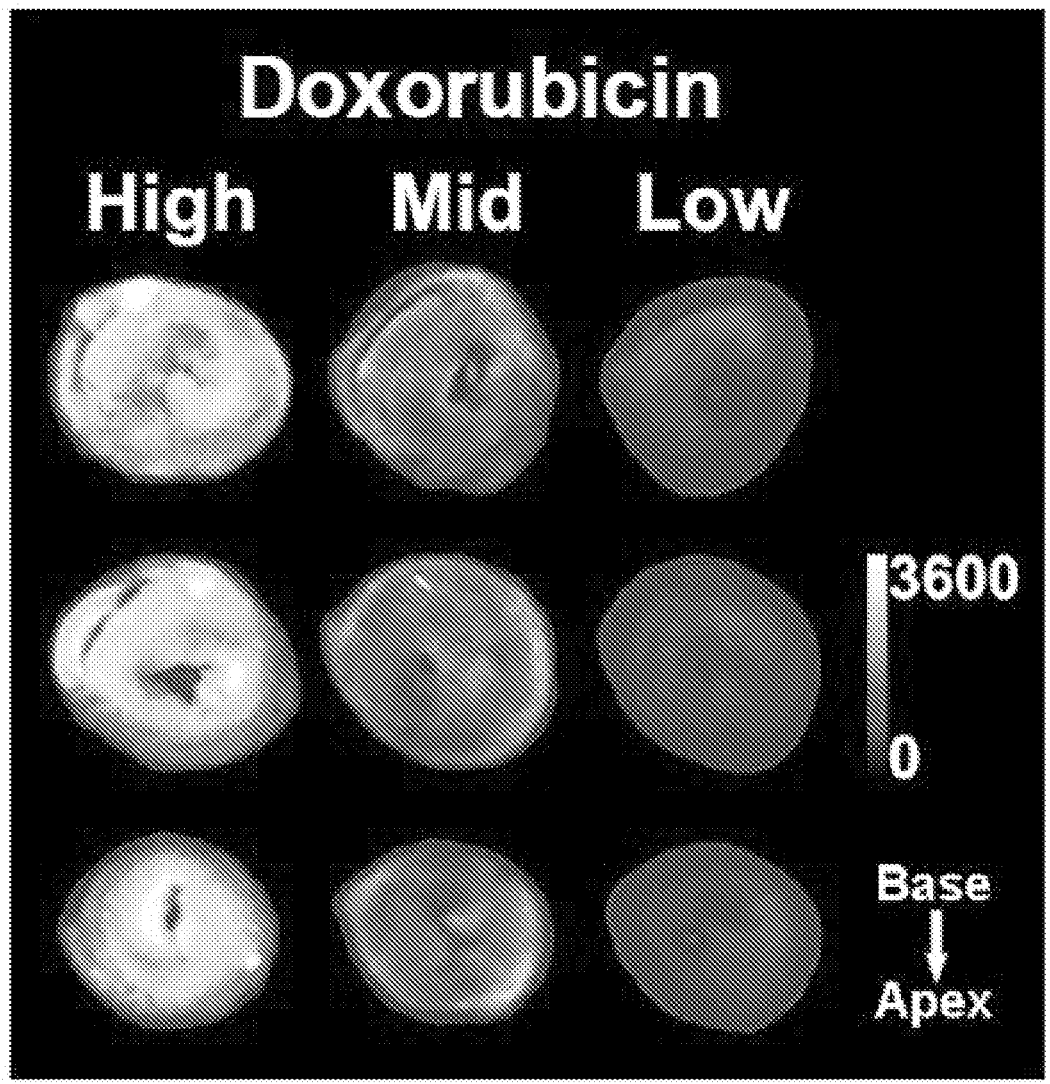
FIG. 1B is an image showing representative ex vivo short-axis heart slices of mouse hearts showing differential DOX uptake 24 hours after a 15 mg/kg DOX injection.
Figure 1C:
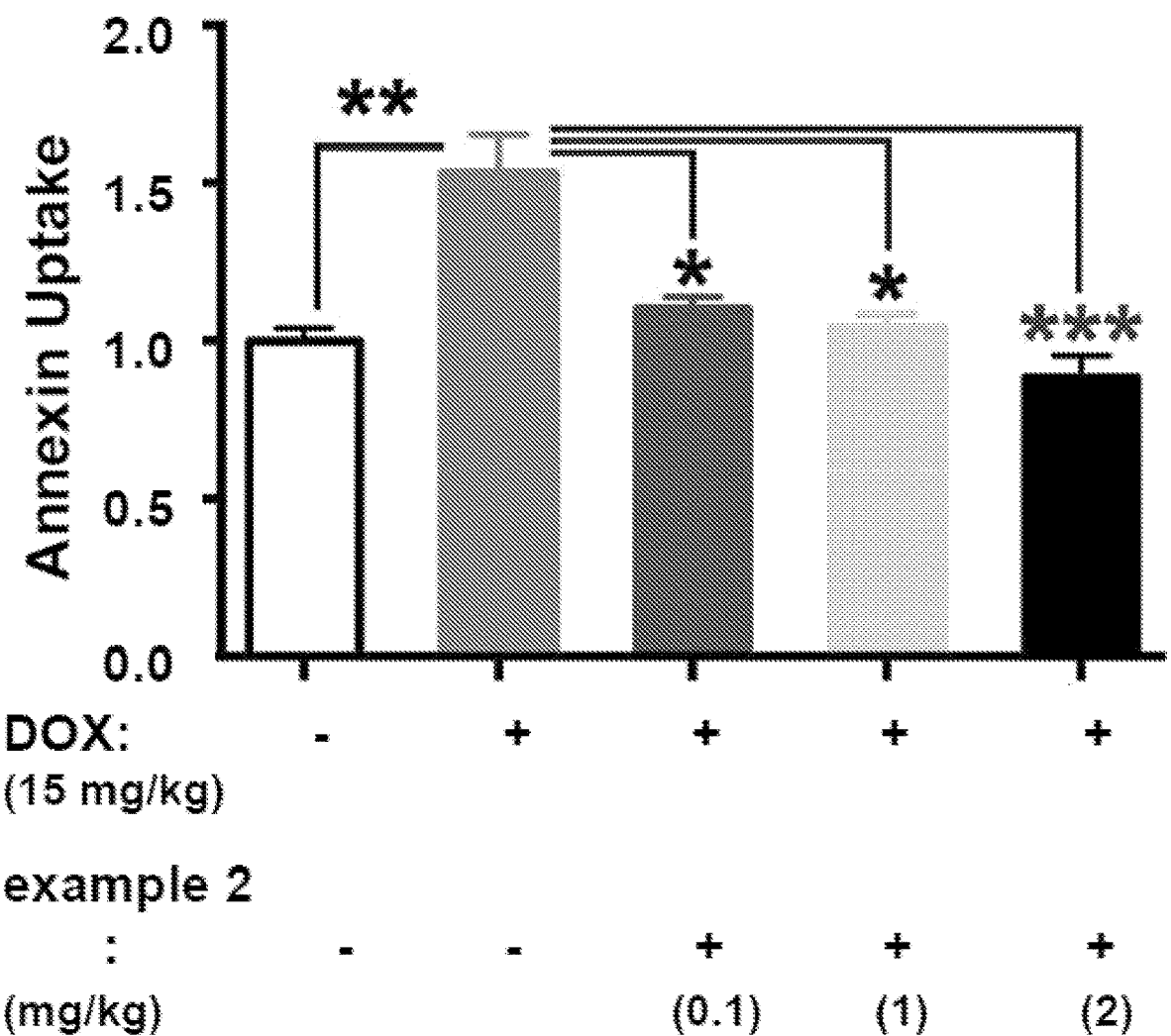
FIG. 1C is a bar graph showing that cardiac annexin uptake increased significantly in the DOX only group (DOX+carrier) compared to the control mice injected with saline and to mice treated with DOX+compound of example 2 at doses of 0.1 mg/kg, 1 mg/kg, and 2 mg/kg.
Figure 1D:
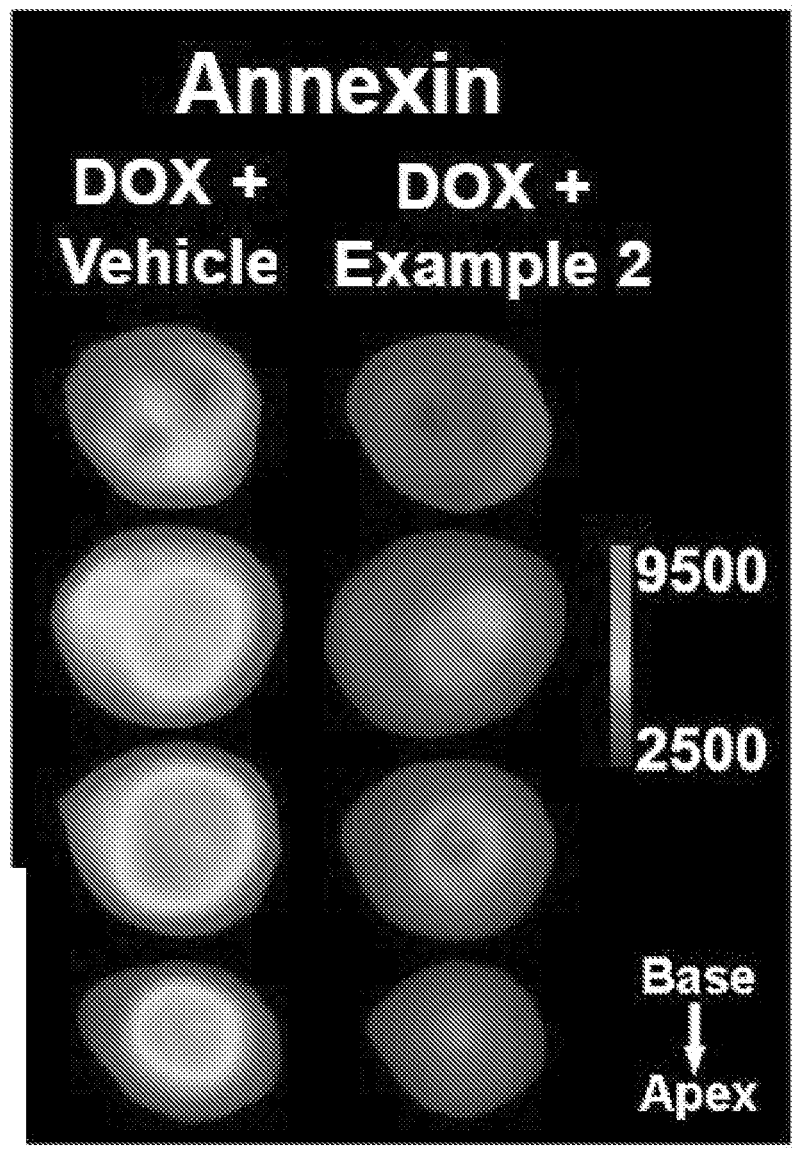
FIG. 1D is an image showing ex vivo Anx-750 accumulation and marked reduction in Anx fluorescence after treatment with the compound of example 2 at a dose of 2 mg/kg.
Figure 10:
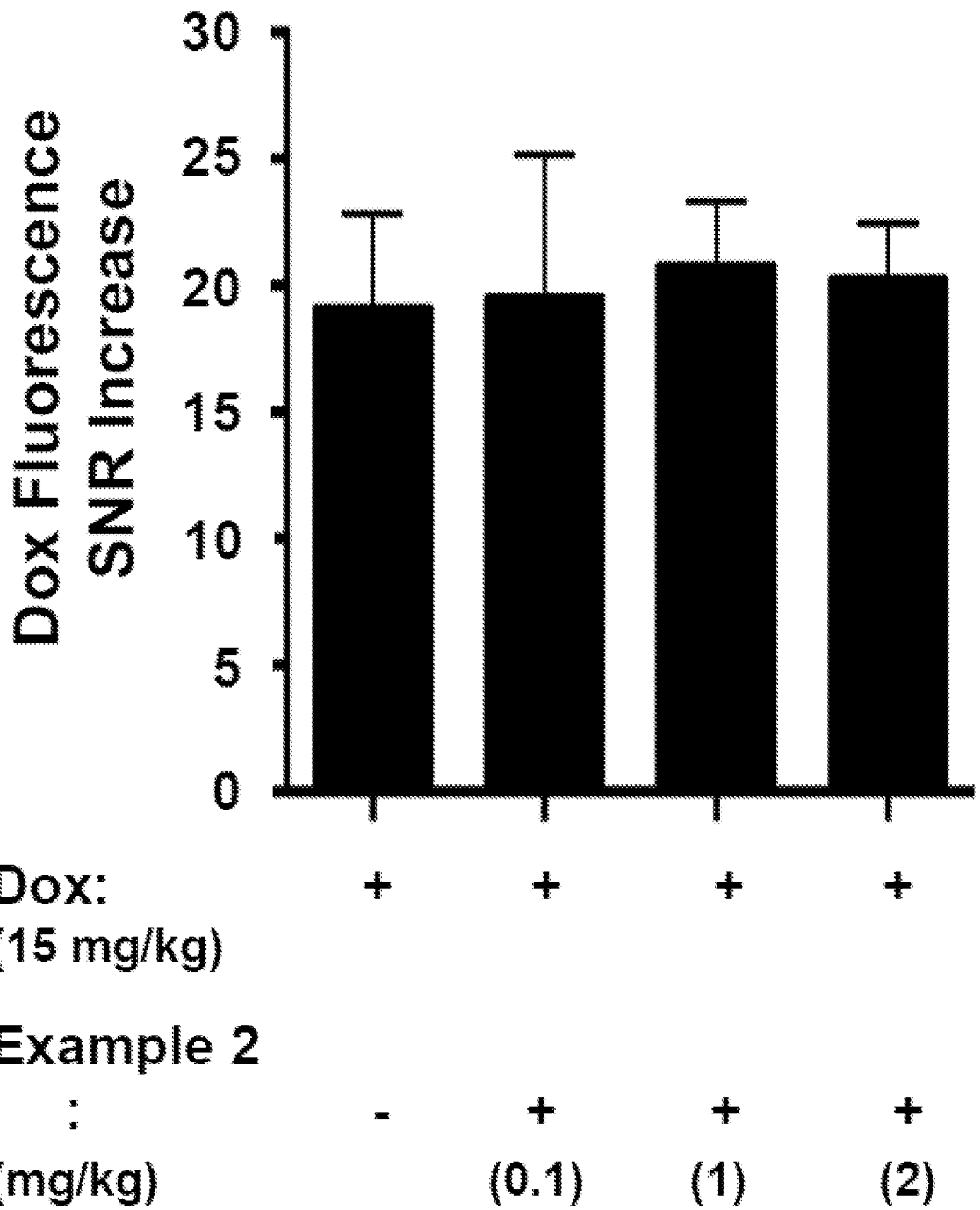
FIG. 10 is a bar graph showing DOX retention in the heart of mice assessed by direct reflectance fluorescence imaging, and quantified as an increase in signal to noise ratio (SNR) compared to the control mice without doxorubicin injection. Doxorubicin fluorescence was consistently high in all cohorts analyzed. No significant difference in DOX fluorescence increase was seen between the DOX only, and any of the mice treated with compound of Example 2. p>0.05, ANOVA. Veh=10% DMSO.

Inherent DOX fluorescence intensity increased linearly with increasing DOX concentration (FIG. 1A). DOX uptake in the heart was quantifiable and ensured that therapeutic impact was examined only in the hearts in which DOX retention was confirmed (FIG. 1B). Compound of Example 2 significantly reduced Annexin-Vivo fluorescence in the mouse heart at concentrations as low as 0.1 mg/kg by intraperitoneal (i.p.) injection (FIGS. 1C and 1D). DOX retention in the heart was consistently high in all the cohorts analyzed (FIG. 10). The potency observed with compound of Example 2 was 250-fold higher than with visnagin in reducing DOX-induced cardiomyocyte apoptosis, consistent with the increased potency observed in the zebrafish assay.

Example 9—Visnagin and Compound of Example 2 Inhibit Induction of CYP1 and Activation of AHR by Doxorubicin Expression levels of the Cyp1 enzymes in treated and untreated zebrafish, and percent rescue form DOX cardiomyopathy in zebrafish co-treated with inhibitors of CYP1 and AHR, and an AHR agonist methyl 2-(1H-indole-3-carbonyl)-1,3-thiazole-4-carboxylate (ITE), were determined as described under the materials and methods section. Results of these experiments are shown in FIGS. 2A-2D. Referring to FIGS. 2A-2D, data are depicted as percent rescue from the doxorubicin cardiomyopathy phenotype (mean and standard deviation). * p<0.05. ** p<0.01.

Figure 2A:
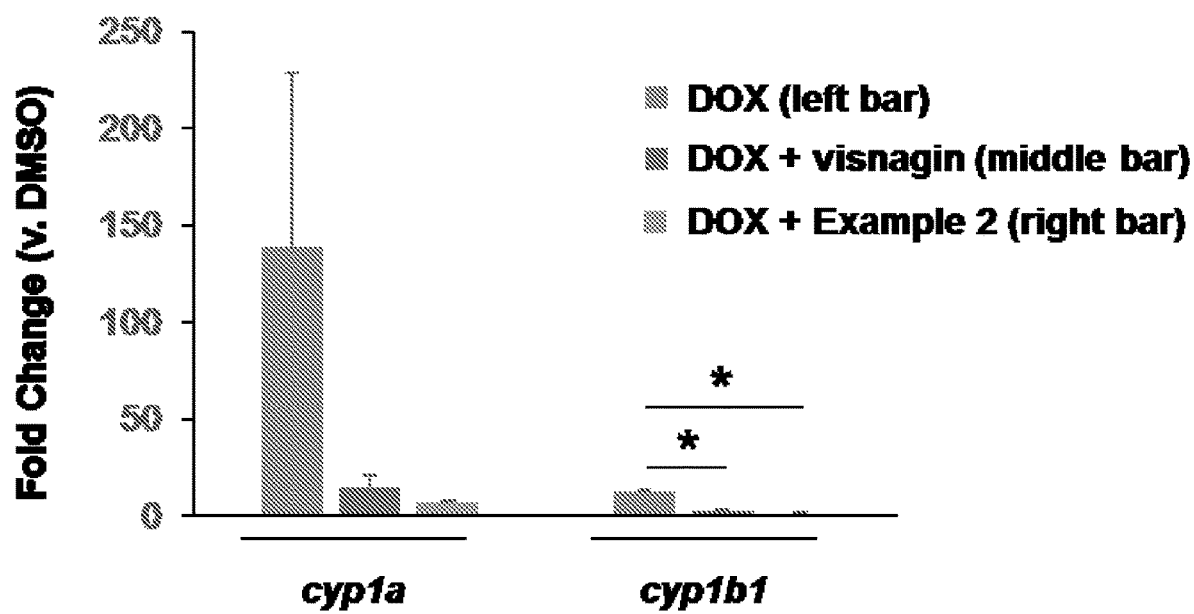
FIG. 2A is a bar graph Expression levels of CYP1A and CYP1B1 in zebrafish treated with DOX, DOX+visnagin (10 µM), and DOX+Example 2 (10 µM), as measured 18 hours post-treatment (prior to the development of the cardiomyopathy phenotype). Data are depicted as mean+/−standard deviation. * p<0.05.
Figure 2B:
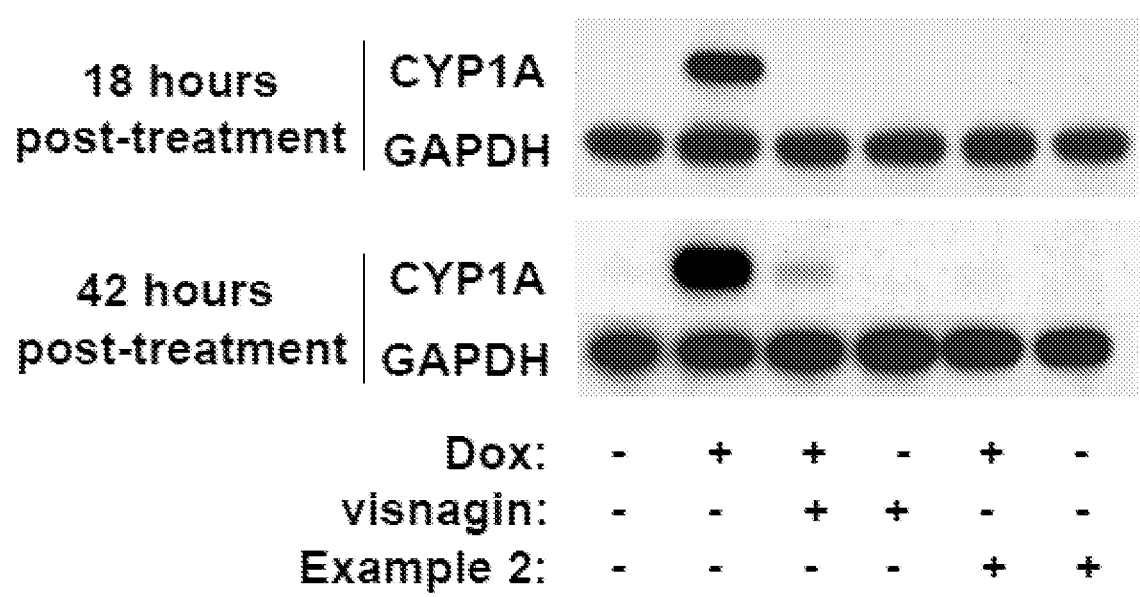
FIG. 2B is an image showing western blotting of fish tissue lysate using a zebrafish-specific CYP1A antibody. Visnagin and Example 2 were each administered at a concentration of 10 µM.

Assessing RNA and protein levels was performed using quantitative PCR (FIG. 2A) and Western blot with a zebrafish-specific antibody against CYP1A (FIG. 2B). Co-treatment with Example 2 mitigated induction of CYP1A as assessed by Western blot more effectively than co-treatment with visnagin. This effect was seen as early as 18 hours post-treatment, prior to the development of the cardiomyopathy phenotype at 42 hours post-treatment.

Figure 2C:
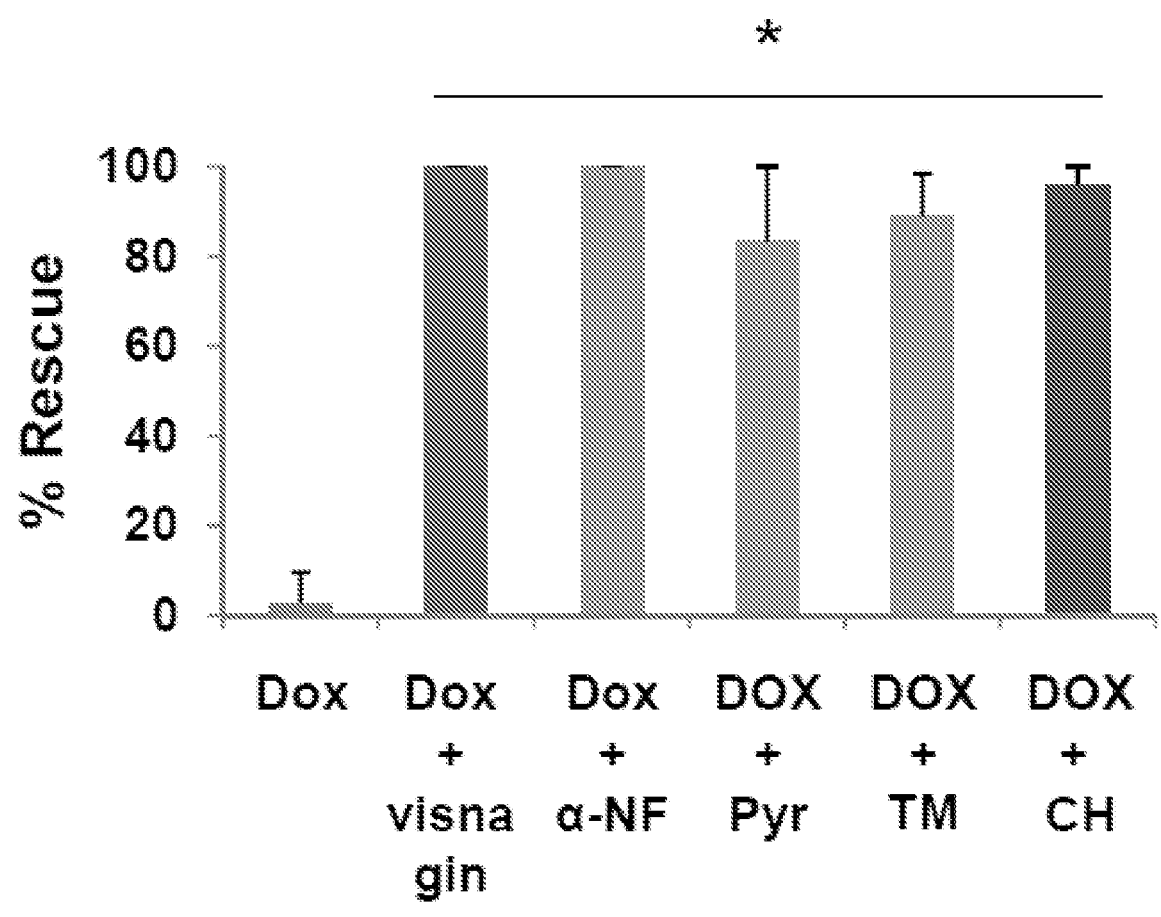
FIG. 2C is a bar graph showing percent rescue from the doxorubicin cardiomyopathy phenotype in zebrafish co-treated with inhibitors of CYP1 and AHR. All inhibitors were administered at a dose of 10 µM. Data are depicted as percent rescue from the doxorubicin cardiomyopathy phenotype (mean and standard deviation). α-NF: α-naphthoflavone; Pyr: pyrene; TM: 2,4,3',5'-tetramethoxystilbene; CH: CH-233191.
Figure 2D:
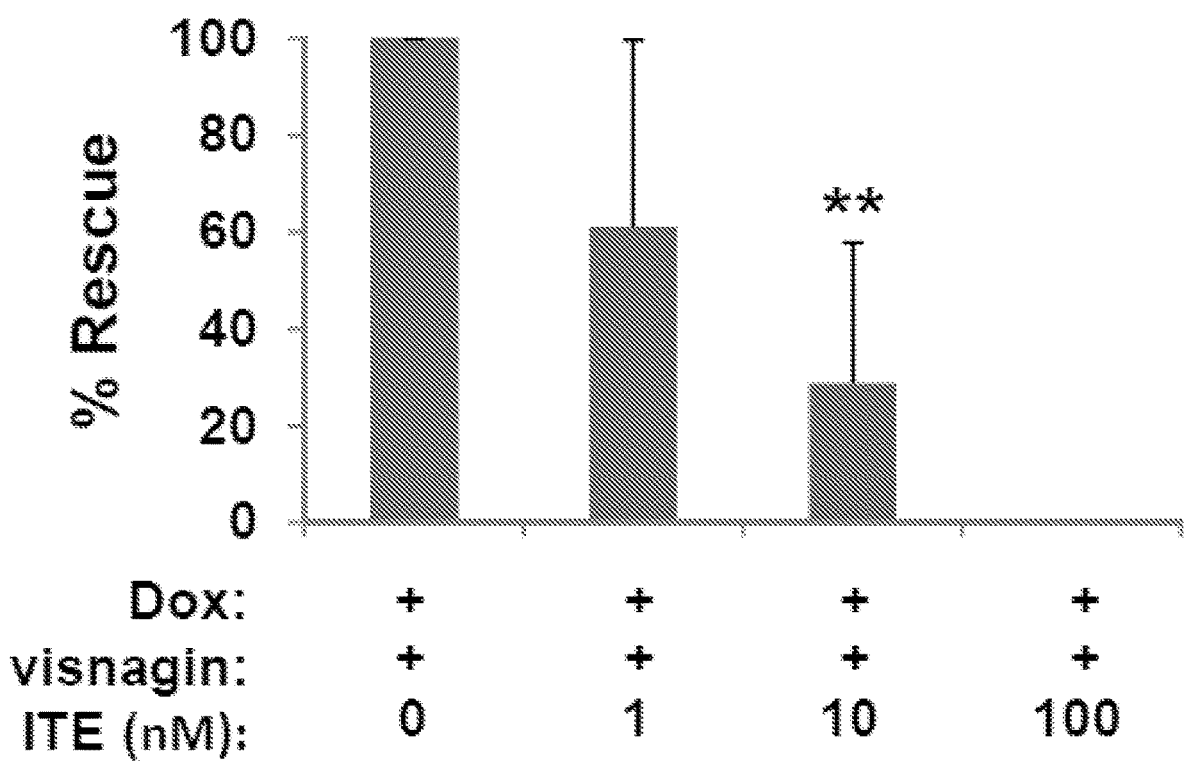
FIG. 2D is a bar graph showing percent rescue from the doxorubicin cardiomyopathy phenotype in zebrafish co-treated with visnagin at 20 µM and the AHR agonist methyl 2-(1H-indole-3-carbonyl)-1,3-thiazole-4-carboxylate (ITE).
Figure 3:
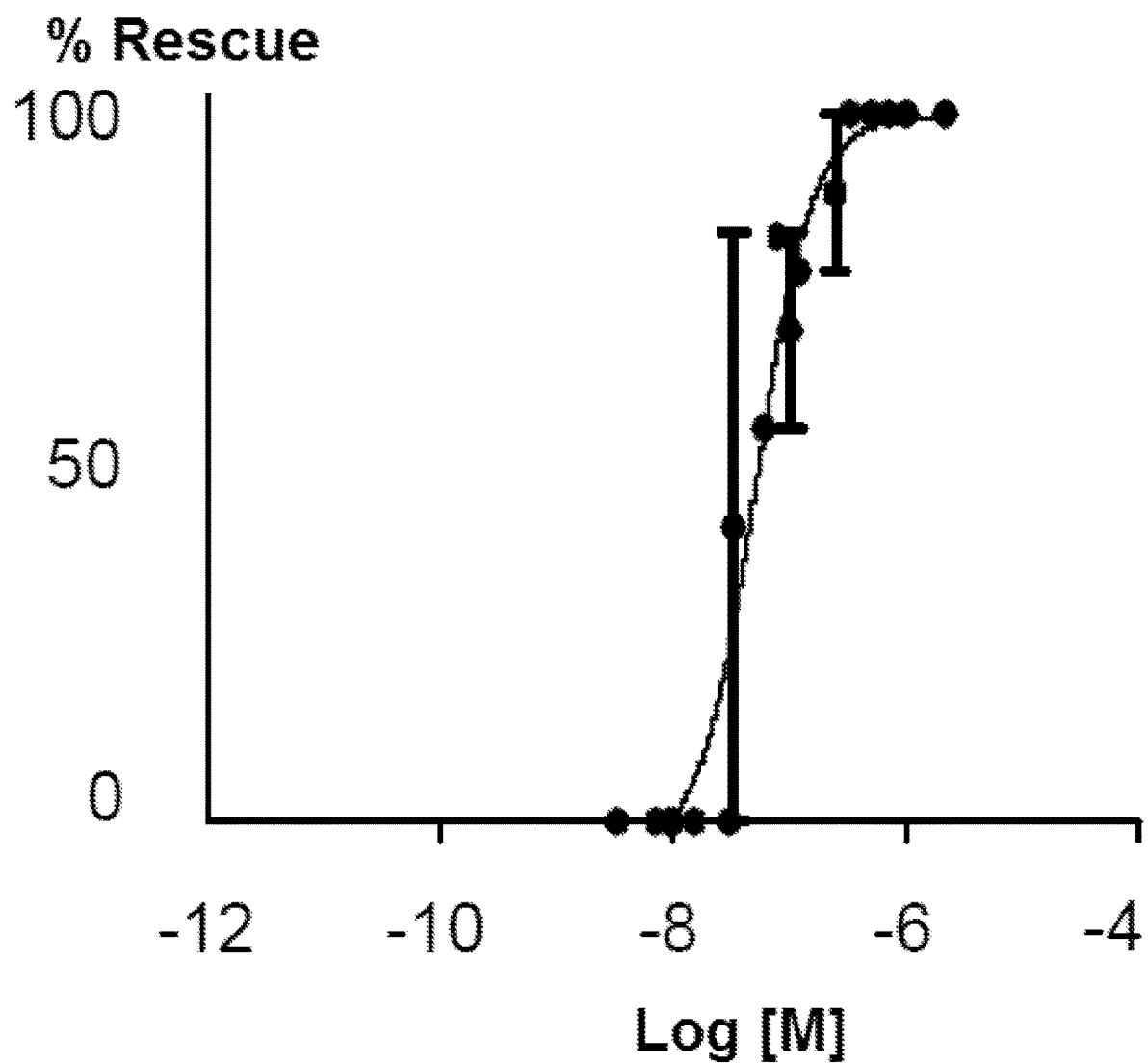
FIG. 3 is a line plot showing in vivo dose-response curve for the rescue of the zebrafish cardiomyopathy phenotype by the compound of example 1.
Figure 4:
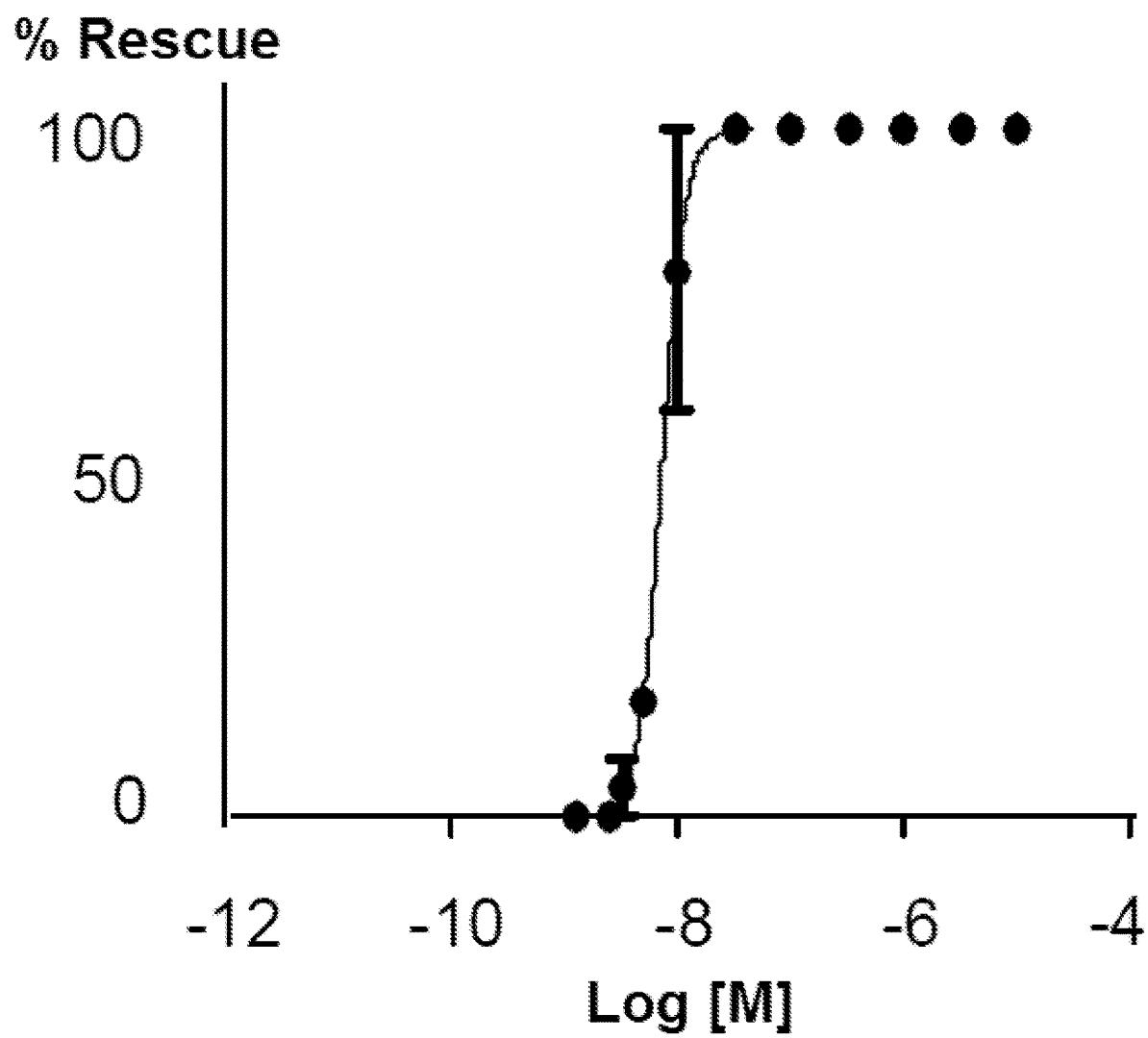
FIG. 4 is a line plot showing in vivo dose-response curve for the rescue of the zebrafish cardiomyopathy phenotype by the compound of example 2.
Figure 5:
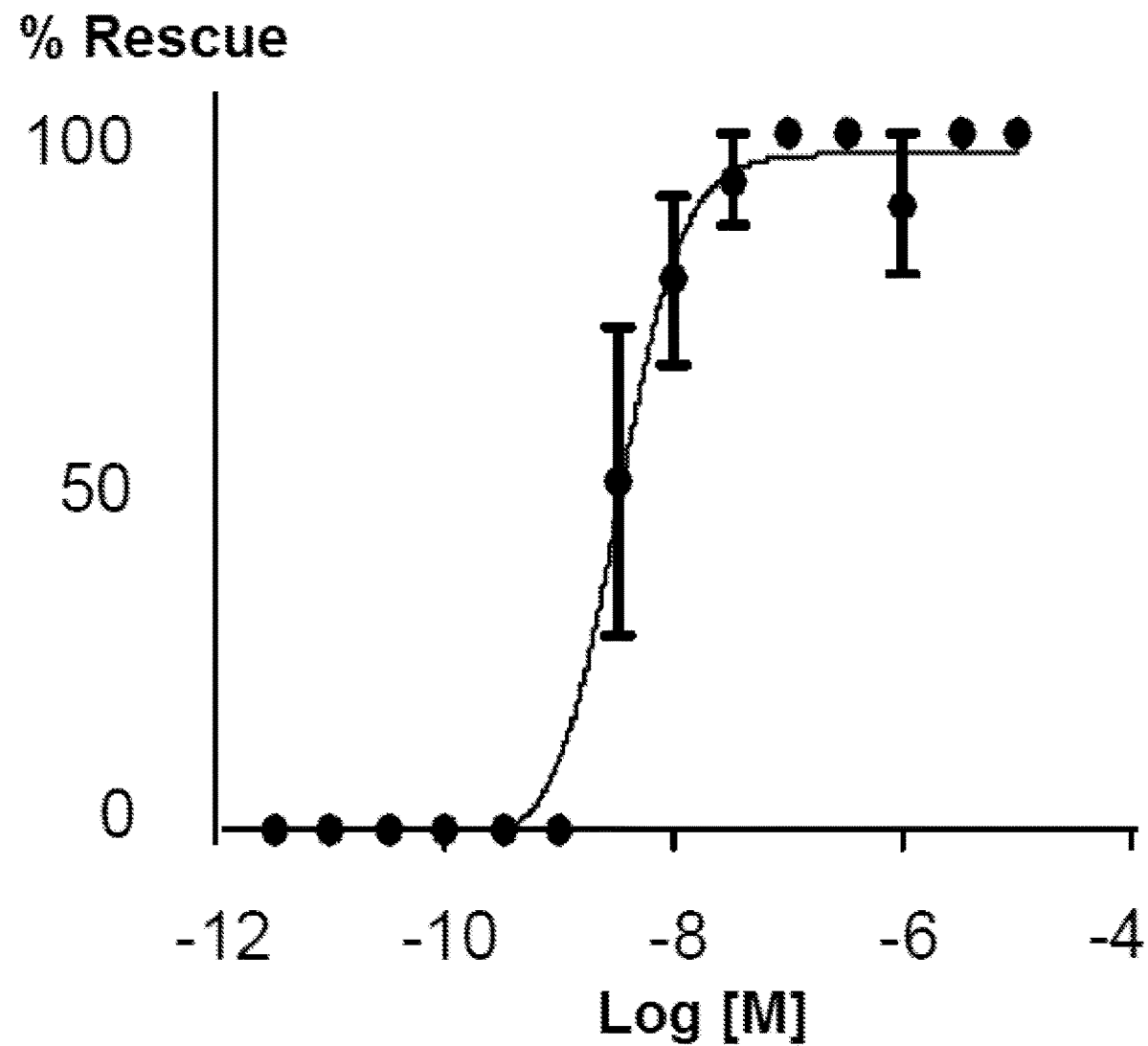
FIG. 5 is a line plot showing in vivo dose-response curve for the rescue of the zebrafish cardiomyopathy phenotype by the compound of example 3.
Figure 6:
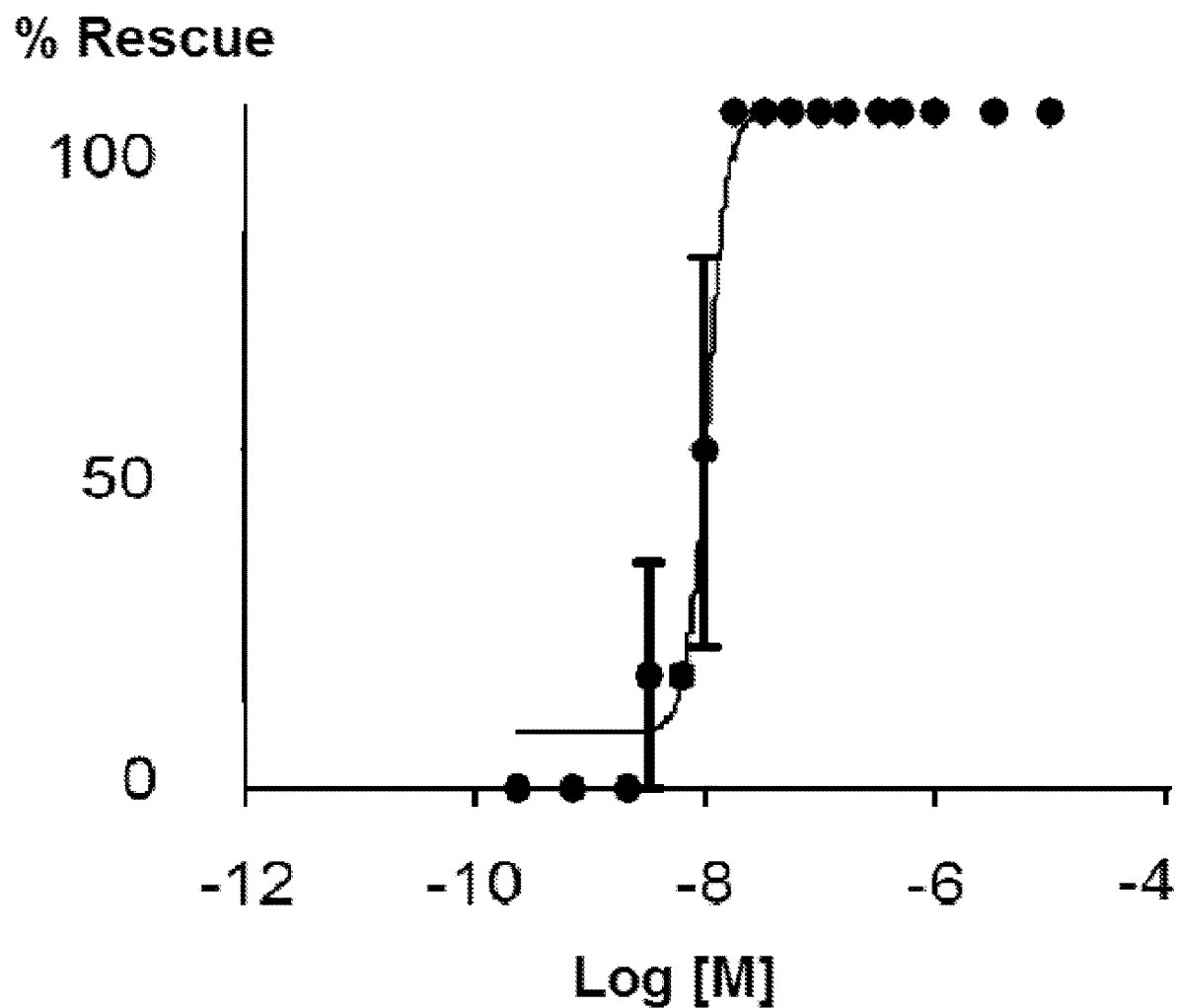
FIG. 6 is a line plot showing in vivo dose-response curve for the rescue of the zebrafish cardiomyopathy phenotype by the compound of example 4.
Figure 7:
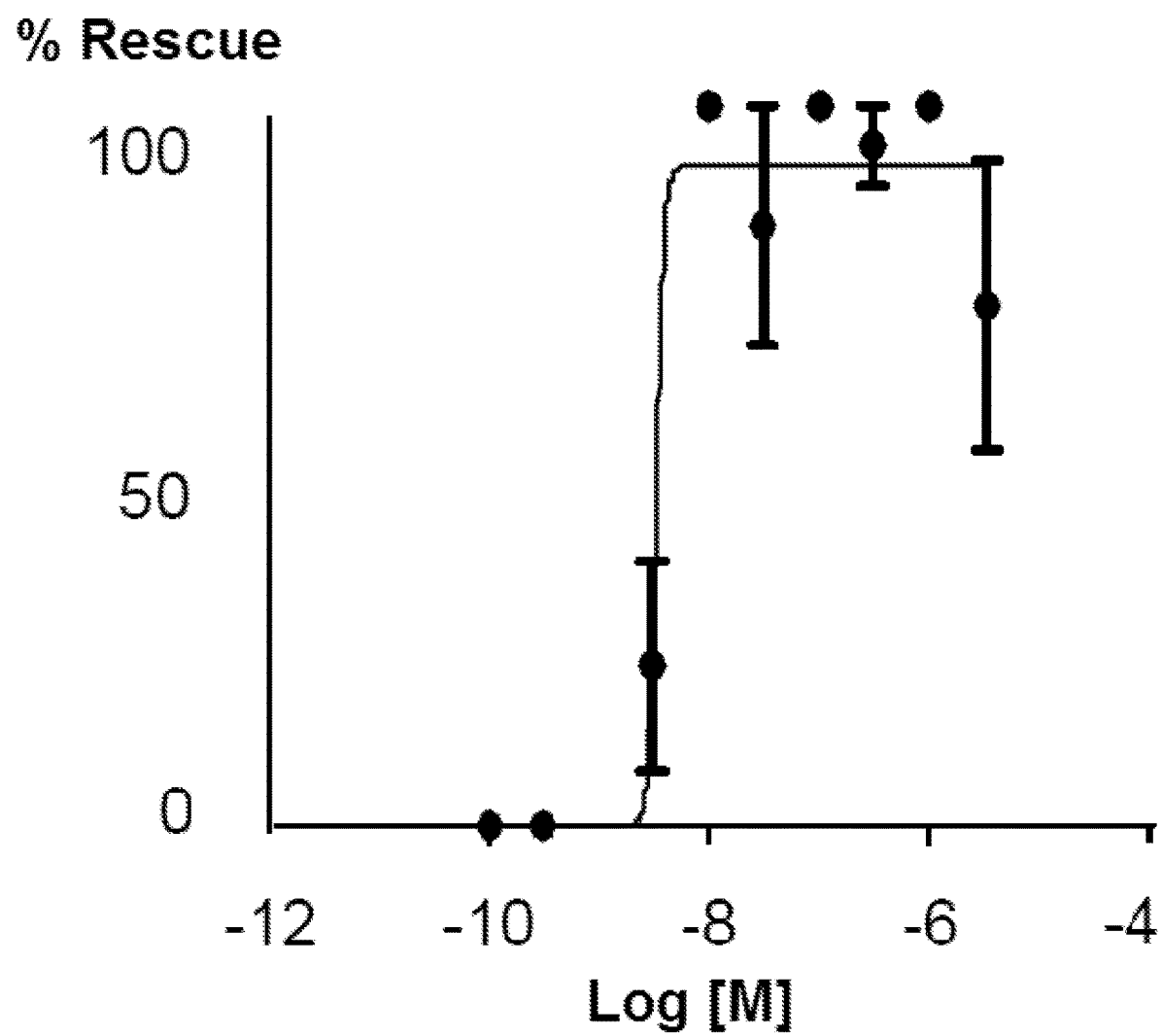
FIG. 7 is a line plot showing in vivo dose-response curve for the rescue of the zebrafish cardiomyopathy phenotype by the compound of example 5.
Figure 8:
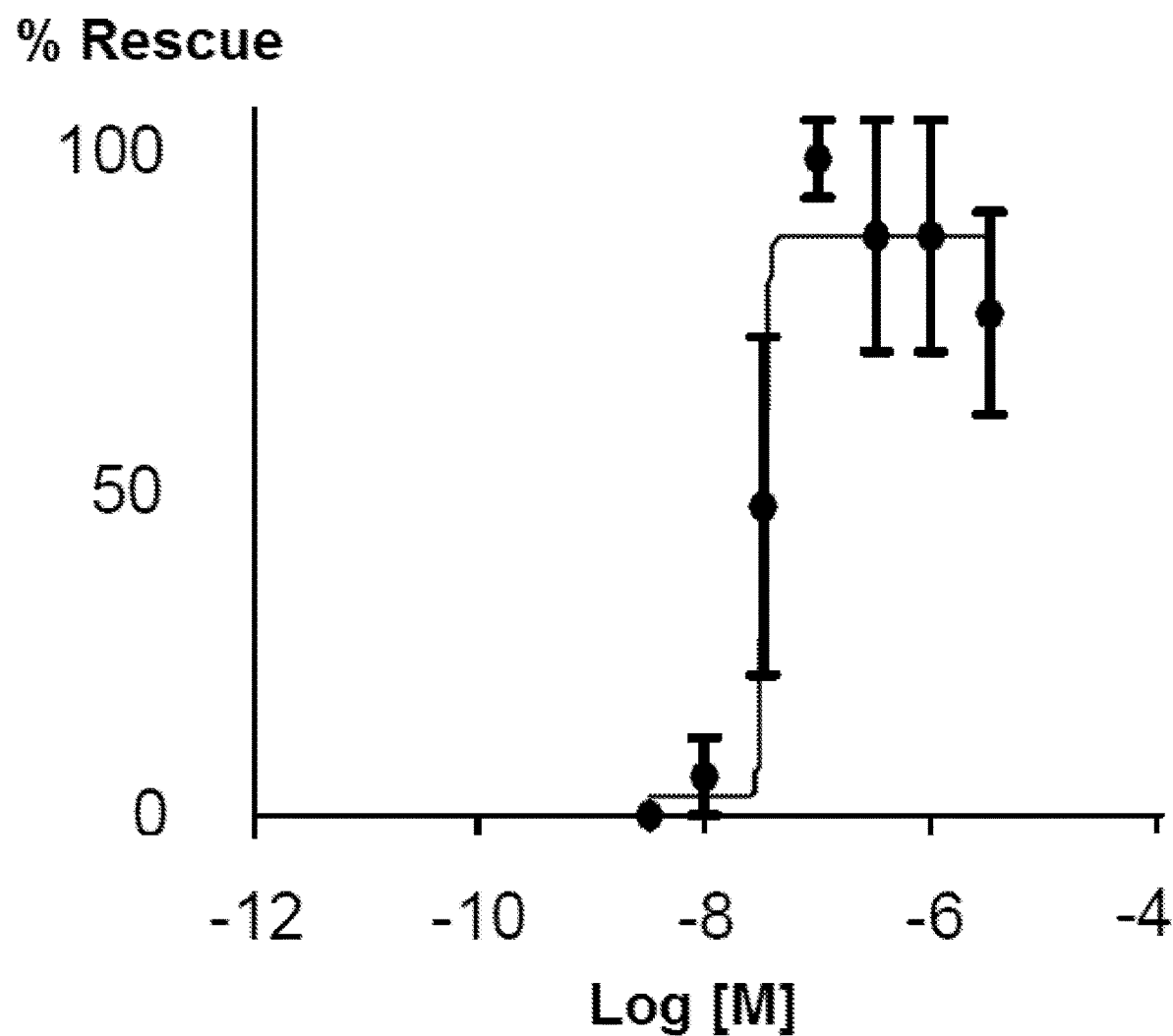
FIG. 8 is a line plot showing in vivo dose-response curve for the rescue of the zebrafish cardiomyopathy phenotype by the compound of example 6.
Figure 9:
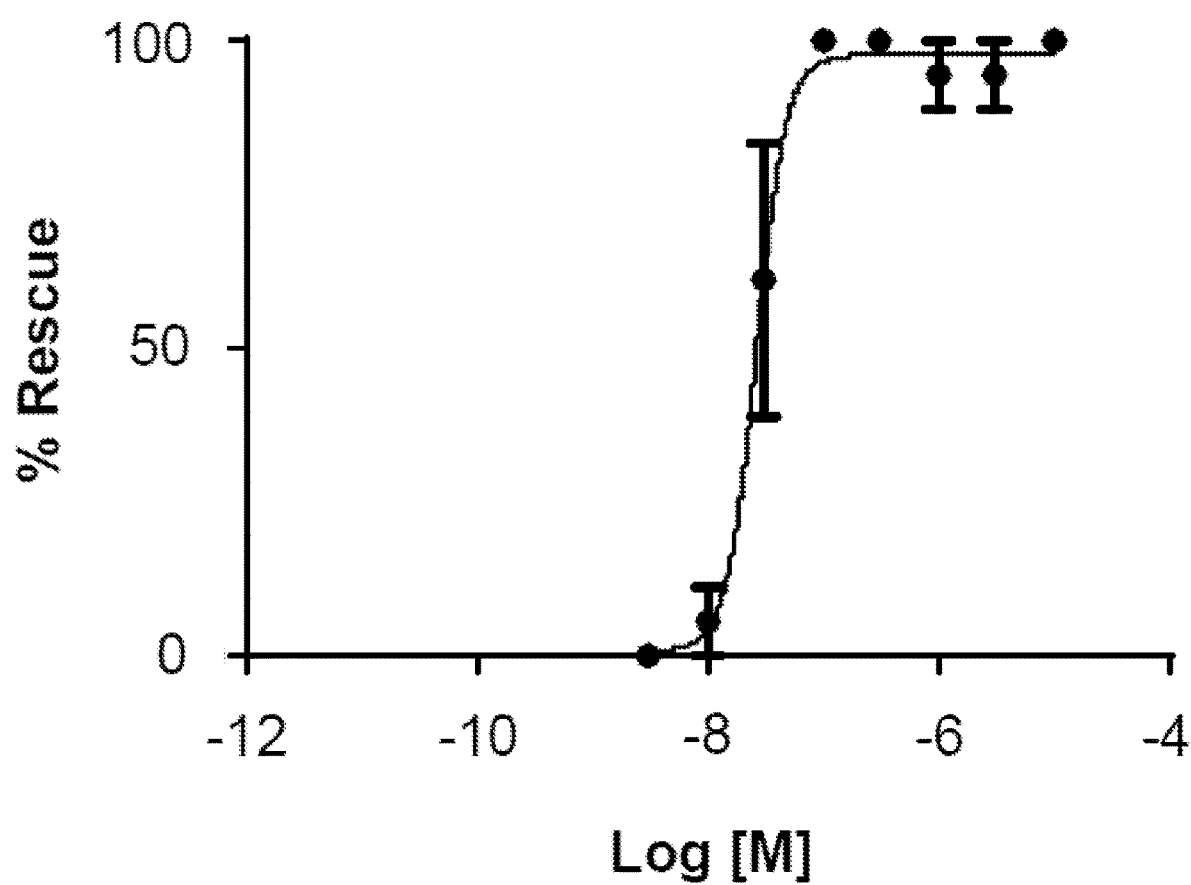
FIG. 9 is a line plot showing in vivo dose-response curve for the rescue of the zebrafish cardiomyopathy phenotype by the compound of example 7.

Treatment with doxorubicin has been shown to activate the aryl hydrocarbon receptor (AHR), a transcriptional regulator which translocates to the nucleus to induce expression of the CYP1 family of enzymes (Volkova et al., 2011). Zebrafish treated with DOX also demonstrated induction of DHRS13L1, THBS1B, and GSTP2, expression levels of which have been previously reported to correlate with AHR activity (Dabir et al., 2008; Goodale et al., 2015; Van Tiem and Di Giulio, 2011). Hence, the compounds of Formulae (I)-(III) may serve as AHR antagonists. Zebrafish was treated with doxorubicin and CYP1 family inhibitors α-naphthoflavone, pyrene, and 2,4,3',5'-tetramethoxystilbene (Liu et al., 2013) or the AHR inhibitor CH-233191. Each treatment resulted in significant rescue from the cardiomyopathy phenotype (FIG. 2C). Rescue from doxorubicin-induced cardiomyopathy mediated by visnagin was abrogated when fish were also treated with the endogenous AHR agonist methyl 2-(1H-indole-3-carbonyl)-1,3-thiazole-4-carboxylate (TIE; FIG. 2D). ITE itself was not toxic when administered to zebrafish embryos without doxorubicin.

Example 10—Proteomics Analysis of Zebrafish Treated with DOX, DOX+Visnagin, or Visnagin The proteomics analysis was carried out as described in the material and methods section. The differentially regulated proteins in zebrafish treated with DOX versus DOX+visnagin are shown in Table 10-1. All protein abundance values are normalized to DMSO-treated control zebrafish. * $p<0.05$ compared to the DMSO control using the Benjamini-Hochberg method of correcting for multiple hypotheses.

TABLE 10-1

| Gene | Protein Abundance (Normalized to DMSO) | | | |
|---|---|---|---|---|
| | DOX | visnagin | DOX + visnagin | DOX/DOX+ visnagin |
| cyp1c1 | 7.91* | 0.80 | 1.05 | 7.57 |
| cyp1a | 9.52* | 0.84 | 1.35* | 7.03 |
| cyp1b1 | 6.26* | 0.94 | 1.18 | 5.31 |
| dhrs13l1 | 3.02* | 0.89 | 1.08 | 2.79 |
| rad9a | 2.92* | 1.15 | 1.17 | 2.50 |
| sqstm1 | 2.78* | 0.98 | 1.14 | 2.43 |
| thbs1b | 2.29* | 0.89 | 0.96 | 2.39 |
| LOC100332237 | 3.03* | 0.96 | 1.30 | 2.34 |
| slc2a1a | 1.19 | 0.83 | 0.53* | 2.23 |
| gstp2 | 2.32* | 0.89 | 1.08 | 2.14 |

Expression levels of 6085 proteins were measured in zebrafish treated with doxorubicin with or without visnagin. Zebrafish treated with doxorubicin alone demonstrated significant upregulation of the CYP1 family of enzymes (CYP1A, CYP1B1, and CYP1C$_1$), whereas zebrafish co-treated with doxorubicin and visnagin showed significantly less CYP1 induction (Table 10-1). This is in contrast to other proteins that were modulated to a similar extent in fish treated with doxorubicin but were not reversed by co-treatment with visnagin. For instance, levels of myosin heavy chain B (MYHB) were decreased in fish treated with DOX alone and in fish treated with DOX+visnagin. Downregulation of MYHB has been previously described with DOX treatment (Ito H, PNAS 1990). Likewise, the inflammatory marker C-reactive protein 3 (CRP3) was increased in both DOX and DOX+visnagin-treated fish. These observations support the specificity of CYP1 downregulation by visnagin and the compounds of Formula (I)-(III) herein and suggest that these compounds do not confer cardioprotection by simply preventing DOX entry into the cell.

Example 11—Inhibition of CYP Enzyme Activity In Vitro by Visnagin and the Compound of Example 2

The ability of the tested compounds to inhibit a panel of CYP enzymes in vitro was assessed using a series of human liver microsome assays. Half-maximal inhibitory concentration ($IC_{50}$) was calculated for compounds demonstrating mean inhibition greater than 50% compared to a reference inhibitor (see materials and methods section). Results of the CYP inhibition experiments are shown in Table 11-1.

TABLE 11-1

| | visnagin | | Example 2 | |
|---|---|---|---|---|
| Cytochrome P450 Enzyme | Mean % Inhibition | $IC_{50}$ (M) | Mean % Inhibition | $IC_{50}$ (M) |
| CYP1A | 94.5 | $2.4 \times 10^{-7}$ | 73.4 | $1.6 \times 10^{-6}$ |
| CYP2B6 | −4.3 | | 67.2 | $8.8 \times 10^{-5}$ |
| CYP2C8 | 8.1 | | 7.1 | |
| CYP2C9 | 1.7 | | 2.4 | |
| CYP2C19 | 1.2 | | 57.0 | $1.2 \times 10^{-5}$ |
| CYP2D6 | 9.9 | | 84.4 | $2.0 \times 10^{-6}$ |
| CYP3A | 4.2 | | 62.7 | $9.3 \times 10^{-6}$ |

Example 2 inhibited a broad range of CYP enzymes at micromolar concentrations, although visnagin was a more potent inhibitor of CYP1A (Table 11-1). This shared inhibitory activity against CYP1A supports the potential role of CYP1 enzymes in cardioprotection mediated by visnagin and Example 2. However, these data also suggest that increased potency of Example 2 as a cardioprotectant does not arise solely from direct inhibition of CYP1A activity. Example 2 was significantly more potent than other previously published CYP1 inhibitors in the zebrafish DOX model, including α-naphthoflavone ($EC_{50}$ 293 nM), pyrene ($EC_{50}$ 3.7 μM), and 2,4,3',5'-tetramethoxystilbene ($EC_{50}$ 8.6 μM). Several factors may contribute to increased potency of Example 2, including improved delivery to the site of action, inhibition of other CYP enzymes, or suppression of CYP1 gene expression, potentially due to direct effects on AHR-mediated transcription.

Example 12—Potency of Tested Compounds in Zebrafish and Cultured BL-1 Cardiomyocytes In Vivo Dose-Response Curves for Tested Compounds Zebrafish were treated with DOX and assessed for the development of the cardiomyopathy phenotype (decreased cardiac contraction, pericardial edema, and decreased tail blood flow). Zebrafish were considered to be rescued if all three features of the cardiomyopathy phenotype were absent upon co-treatment with a tested compound. Results of these experiments are presented in FIGS. 3-9. Referring to FIGS. 3-9, data are depicted as mean+/−standard error (n=6 fish per dose; each experiment performed in triplicate).

HL-1 Cardiomyocytes

Compounds were tested in HL-1 cultured cardiomyocytes to assess for efficacy in preventing DOX-induced apoptosis. Cell viability was assessed as described in the materials and methods section.

Results of the potency tests are shown in Table 12-1.

TABLE 12-1

| Example | EC$_{50}$ is zebrafish | EC$_{50}$ in HL-1 Cells |
|---|---|---|
| 1 | 52 nM | >50 µM |
| 2 | 7 nM | >50 µM |
| 3 | 3 nM | >50 µM |
| 4 | 10 nM | >50 µM |
| 5 | 3 nm | |
| 6 | 33 nM | >50 µM |
| 7 | 258 nm | |

Tested compounds that were potent in the zebrafish model of doxorubicin cardiotoxicity were ineffective at doses up to 50 µM in cultured HL-1 cardiomyocytes. For instance, Example 2 had an EC$_{50}$ of 7 nM in the zebrafish model and was cardioprotective at a dose of 0.1 mg/kg in the mouse model, but was ineffective in the HL-1 cell culture model. This suggests that the tested compounds may be prodrugs that require in vivo metabolism in order to confer cardioprotection, or that they are cardioprotective by exerting action at a location other than the cardiomyocyte.

The experiments described herein showed that DOX causes robust induction of Cytochrome P450 family 1 (CYP1) that was mitigated by visnagin (4-ethoxy-7-methyl-5H-furo[3,2-g][1]-benzopyran-5-one, CAS Registry No. 82-57-5) and the compounds of Formulae (I)-(III) described herein. Treatment with structurally divergent CYP1 inhibitors (e.g., α-naphthoflavone, pyrene, 2,4,3',5'-tetramethoxystilbene, or CH-233191) prevented DOX cardiomyopathy in zebrafish, supporting the finding that CYP1 is an important contributor to DOX cardiotoxicity (see Example 9, FIGS. 2A-2D).

In the zebrafish model of doxorubicin cardiotoxicity, the tested compounds of Formula (I)-(III) containing a hydrolyzable carbamate group increased the potency of visnagin up to 1000-fold without evidence of toxicity. The carbamate group increases delivery of tested compounds to their site of action, where esterases and other enzymes may participate in bioconversion and release of the active metabolite.

In zebrafish, doxorubicin treatment significantly increased levels of CYP1 enzymes, an effect that was reduced by visnagin and completely abolished by Example 2. Moreover, three structurally different CYP1 inhibitors as well as an AHR inhibitor all protected against doxorubicin cardiotoxicity in the zebrafish model. Of note, inhibitors of other CYP enzymes (e.g., CYP3A4) did not confer cardioprotection in this model. These observations suggest that visnagin and the compounds of Formulae (I)-(III) protect against cardiotoxicity by suppressing doxorubicin-mediated CYP1 induction, in addition to direct inhibition of CYP1 enzyme activity. The compounds of Formulae (I)-(III) are nearly 1000-fold more potent in zebrafish and 250-fold more potent in mice when compared to visnagin.

CYP1 may play a role in estrogen-mediated tumor formation (Bruno and Njar, 2007). Also, CYP1 enzymes are important in the metabolism of arachidonic acid (Divanovic et al., 2013), which has been previously implicated in doxorubicin cardiotoxicity (Maayah et al., 2016). Although all CYP1 family members are expressed in extrahepatic tissues, CYP1B1 in particular is overexpressed in a wide range of tumors including breast cancer (Murray et al., 1997). Notably, CYP1B1 catalyzes C-4 hydroxylation of estradiol, a process which has been implicated in estrogen-related tumorigenesis (Liehr and Ricci, 1996). Hence, CYP1 inhibition may simultaneously confer cardioprotection while enhancing doxorubicin's anti-tumor effect, increasing its appeal as a chemotherapeutic strategy.

REFERENCES

1. Asselin, B. L., Devidas, M., Chen, L., Franco, V. I., Pullen, J., Borowitz, M. J., Hutchison, R. E., Ravindranath, Y, Armenian, S. H., Camitta, B. M., et al. (2016). Cardioprotection and Safety of Dexrazoxane in Patients Treated for Newly Diagnosed T-Cell Acute Lymphoblastic Leukemia or Advanced-Stage Lymphoblastic Non-Hodgkin Lymphoma: A Report of the Children's Oncology Group Randomized Trial Pediatric Oncology Group 9404. Journal of clinical oncology: official journal of the American Society of Clinical Oncology 34, 854-862.
2. Bruno, R. D., and Njar, V. C. (2007). Targeting cytochrome P450 enzymes: a new approach in anti-cancer drug development. Bioorganic & medicinal chemistry 15, 5047-5060.
3. Cardinale, D., Colombo, A., Bacchiani, G., Tedeschi, I., Meroni, C. A., Veglia, F., Civelli, M., Lamantia, G., Colombo, N., Curigliano, G., et al. (2015). Early detection of anthracycline cardiotoxicity and improvement with heart failure therapy. Circulation 131, 1981-1988.
4. Chen, H. H., Josephson, L., and Sosnovik, D. E. (2011). Imaging of apoptosis in the heart with nanoparticle technology. Wiley interdisciplinary reviews Nanomedicine and nanobiotechnology 3, 86-99.
5. Claycomb, W. C., Lanson, N. A., Jr., Stallworth, B. S., Egeland, D. B., Delcarpio, J. B., Bahinski, A., and Izzo, N. J., Jr. (1998). HL-1 cells: a cardiac muscle cell line that contracts and retains phenotypic characteristics of the adult cardiomyocyte. Proceedings of the National Academy of Sciences of the United States of America 95, 2979-2984.
6. Dabir, P., Marinic, T. E., Krukovets, I., and Stenina, O. I. (2008). Aryl hydrocarbon receptor is activated by glucose and regulates the thrombospondin-1 gene promoter in endothelial cells. Circulation research 102, 1558-1565.
7. Divanovic, S., Dalli, J., Jorge-Nebert, L. F., Flick, L. M., Galvez-Peralta, M., Boespflug, N. D., Stankiewicz, T. E., Fitzgerald, J. M., Somarathna, M., Karp, C. L., et al. (2013). Contributions of the three CYP1 monooxygenases to pro-inflammatory and inflammation-resolution lipid mediator pathways. Journal of immunology 191, 3347-3357.
8. Ghosh, A. K., and Brindisi, M. (2015). Organic carbamates in drug design and medicinal chemistry. Journal of medicinal chemistry 58, 2895-2940.
9. Goldstone, J. V, McArthur, A. G., Kubota, A., Zanette, J., Parente, T., Jonsson, M E., Nelson, D. R., and Stegeman, J. J. (2010). Identification and developmental expression of the full complement of Cytochrome P450 genes in Zebrafish. BMC genomics 11, 643.
10. Goodale, B. C., La Du, J., Tilton, S. C., Sullivan, C. M., Bisson, W. H., Waters, K. M., and Tanguay, R. L. (2015). Ligand-Specific Transcriptional Mechanisms Underlie Aryl Hydrocarbon Receptor-Mediated Developmental Toxicity of Oxygenated PAHs.
Toxicological sciences: an official journal of the Society of Toxicology 147, 397-411.
11. Hasinoff, B. B., and Herman, E. H. (2007). Dexrazoxane: how it works in cardiac and tumor cells. Is it a prodrug or is it a drug? CardiovascToxicol 7, 140-144.
12. Ichikawa, Y, Ghanefar, M., Bayeva, M., Wu, R., Khechaduri, A., Naga Prasad, S. V., Mutharasan, R. K., Naik, T. J., and Ardehali, H. (2014). Cardiotoxicity of doxorubicin is mediated through mitochondrial iron accumulation. The Journal of clinical investigation 124, 617-630.
13. Imondi, A. R. (1998). Preclinical models of cardiac protection and testing for effects of dexrazoxane on doxorubicin antitumor effects. Seminars in oncology 25, 22-30.
14. Imondi, A. R., Della Torre, P., Mazue, G., Sullivan, T. M., Robbins, T. L., Hagerman, L. M., Podesta, A., and Pinciroli, G. (1996). Dose-response relationship of dexrazoxane for prevention of doxorubicin-induced cardiotoxicity in mice, rats, and dogs. Cancer research 56, 4200-4204.
15. Jenkins, C. M., Cedars, A., and Gross, R. W. (2009). Eicosanoid signalling pathways in the heart. Cardiovascular research 82, 240-249.
16. Jonsson, M E., Orrego, R., Woodin, B. R., Goldstone, J. V, and Stegeman, J. J. (2007). Basal and 3,3',4,4',5-pentachlorobiphenyl-induced expression of cytochrome P450 1A, 1B and 1C genes in zebrafish. Toxicology and applied pharmacology 221, 29-41.
17. Liehr, J. G., and Ricci, M. J. (1996). 4-Hydroxylation of estrogens as marker of human mammary tumors. Proceedings of the National Academy of Sciences of the United
States of America 93, 3294-3296.
18. Liu, J., Sridhar, J., and Foroozesh, M. (2013). Cytochrome P450 family 1 inhibitors and structure-activity relationships. Molecules 18, 14470-14495.
19. Liu, Y, Asnani, A., Zou, L., Bentley, V L., Yu, M., Wang, Y, Dellaire, G., Sarkar, K. S., Dai, M., Chen, H. H., et al. (2014). Visnagin protects against doxorubicin-induced cardiomyopathy through modulation of mitochondrial malate dehydrogenase. Science translational medicine 6, 266ra170.
20. Lyu, Y L., Kerrigan, J. E., Lin, C. P., Azarova, A. M., Tsai, Y C., Ban, Y, and Liu, L. F.
(2007). Topoisomerase IIbeta mediated DNA double-strand breaks: implications in doxorubicin cardiotoxicity and prevention by dexrazoxane. Cancer research 67, 8839-8846.
21. Maayah, Z. H., Althurwi, H. N., Abdelhamid, G., Lesyk, G., Jurasz, P., and El-Kadi, A. O. (2016). CYP1B1 inhibition attenuates doxorubicin-induced cardiotoxicity through a mid-chain HETEs-dependent mechanism. Pharmacological research 105, 28-43.
22. Mitani, I., Jain, D., Joska, T. M., Burtness, B., and Zaret, B. L. (2003). Doxorubicin cardiotoxicity: prevention of congestive heart failure with serial cardiac function monitoring with equilibrium radionuclide angiocardiography in the current era. Journal of nuclear cardiology: official publication of the American Society of Nuclear Cardiology 10, 132-139.
23. Murray, G. I., Taylor, M. C., McFadyen, M. C., McKay, J. A., Greenlee, W. F., Burke, M. D., and Melvin, W. T. (1997). Tumor-specific expression of cytochrome P450 CYP1B1. Cancer research 57, 3026-3031.
24. Seif, A. E., Walker, D. M., Li, Y, Huang, Y S., Kavcic, M., Torp, K., Bagatell, R., Fisher, B. T., and Aplenc, R. (2015). Dexrazoxane exposure and risk of secondary acute myeloid leukemia in pediatric oncology patients. Pediatric blood & cancer 62, 704-709.
25. Shimada, T., and Fujii-Kuriyama, Y. (2004). Metabolic activation of polycyclic aromatic hydrocarbons to carcinogens by cytochromes P450 1A1 and 1B1. Cancer science 95, 1-6.
26. Suliman, H. B., Carraway, M. S., Ali, A. S., Reynolds, C. M., Welty-Wolf, K. E., and Piantadosi, C. A. (2007). The CO/HO system reverses inhibition of mitochondrial biogenesis and prevents murine doxorubicin cardiomyopathy. The Journal of clinical investigation 117, 3730-3741.
27. Swain, S. M., Whaley, F. S., Gerber, M. C., Weisberg, S., York, M., Spicer, D., Jones, S. E., Wadler, S., Desai, A., Vogel, C., et al. (1997). Cardioprotection with dexrazoxane for doxorubicin-containing therapy in advanced breast cancer. Journal of clinical oncology: official journal of the American Society of Clinical Oncology 15, 1318-1332.
28. Tebbi, C. K., London, W. B., Friedman, D., Villaluna, D., De Alarcon, P. A., Constine, L. S., Mendenhall, N. P, Sposto, R., Chauvenet, A., and Schwartz, C. L. (2007). Dexrazoxane-associated risk for acute myeloid leukemia/myelodysplastic syndrome and other secondary malignancies in pediatric Hodgkin's disease. Journal of clinical oncology: official journal of the American Society of Clinical Oncology 25, 493-500.
29. Van Tiem, L. A., and Di Giulio, R. T. (2011). AHR2 knockdown prevents PAH-mediated cardiac toxicity and XRE- and ARE-associated gene induction in zebrafish (*Danio rerio*). Toxicology and applied pharmacology 254, 280-287.
30. Volkova, M., *Palmeri*, M., Russell, K. S., and Russell, R. R. (2011). Activation of the aryl hydrocarbon receptor by doxorubicin mediates cytoprotective effects in the heart. Cardiovascular research 90, 305-314.
31. Wallace, K. B. (2003). Doxorubicin-induced cardiac mitochondrionopathy. Pharmacology & toxicology 93, 105-115.
32. Zhang, S., Liu, X., Bawa-Khalfe, T., Lu, L. S., Lyu, Y L., Liu, L. F., and Yeh, E. T. (2012). Identification of the molecular basis of doxorubicin-induced cardiotoxicity. Nature medicine 18, 1639-1642.
33. Zhou, S., Starkov, A., Froberg, M. K., Leino, R. L., and Wallace, K. B. (2001). Cumulative and irreversible cardiac mitochondrial dysfunction induced by doxorubicin. Cancer research 61, 771-777.

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:
1. A pharmaceutical composition comprising a compound of formula:

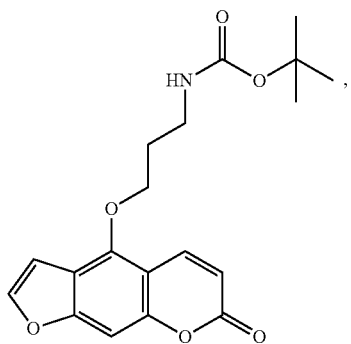 [SMILES: CC(C)(C)OC(=O)NCCCOc1c2ccoc2cc2oc(=O)ccc12]

or a pharmaceutically acceptable salt thereof, and a pharmaceutically acceptable carrier.

2. A method of treating or preventing cardiotoxicity or cardiomyopathy induced by an anthracycline chemotherapeutic agent in a subject, the method comprising administering to the subject in need thereof a therapeutically effective amount of the pharmaceutical composition of claim 1.

3. The method of claim 2, wherein the cardiotoxicity or the cardiomyopathy is characterized by pericardial edema, impaired cardiac contractility, or decreased blood flow through the vasculature.

4. The method of claim 2, wherein the anthracycline chemotherapeutic agent is doxorubicin, or a pharmaceutically acceptable salt thereof.

5. A method of inhibiting induction of a Cytochrome P450 family 1 (CYP1) enzyme in a cardiomyocyte, the method comprising contacting the cardiomyocyte with an effective amount of the pharmaceutical composition of claim 1.

6. The method of claim 5, wherein the Cytochrome P450 family 1 (CYP1) enzyme is induced by contacting the cardiomyocyte with an anthracycline chemotherapeutic agent.

7. A method of inhibiting a Cytochrome P450 family 1 (CYP1) enzyme in a cardiomyocyte, the method comprising contacting the cardiomyocyte with an effective amount of the pharmaceutical composition of claim 1.

8. The method of claim 7, wherein the Cytochrome P450 family 1 (CYP1) enzyme is selected from CYP1A and CYP1B1.

* * * * *